(12) United States Patent
Gruenbacher et al.

(10) Patent No.: US 9,433,696 B2
(45) Date of Patent: Sep. 6, 2016

(54) MICROFLUIDIC DELIVERY SYSTEM FOR RELEASING FLUID COMPOSITIONS

(71) Applicant: The Procter & Gamble Company, Cincinnati, OH (US)

(72) Inventors: Dana Paul Gruenbacher, Fairfield, OH (US); David S Hunt, San Diego, CA (US); Joseph Edward Scheffelin, San Diego, CA (US); Timothy James Hoekstra, Escondido, CA (US); Simon Dodd, West Linn, OR (US); Roberto Brioschi, Sesto San Giovanni (IT)

(73) Assignee: The Procter & Gamble Company, Cincinnati, OH (US)

( * ) Notice: Subject to any disclaimer, the term of this patent is extended or adjusted under 35 U.S.C. 154(b) by 185 days.

(21) Appl. No.: 14/310,401

(22) Filed: Jun. 20, 2014

(65) Prior Publication Data

US 2015/0367016 A1 Dec. 24, 2015

(51) Int. Cl.
*B01F 3/04* (2006.01)
*B05B 17/00* (2006.01)
*A61L 9/14* (2006.01)
*B05B 17/06* (2006.01)
*A45D 34/00* (2006.01)
*B41J 2/00* (2006.01)

(52) U.S. Cl.
CPC .............. *A61L 9/14* (2013.01); *A45D 34/00* (2013.01); *B01F 3/04085* (2013.01); *B05B 17/0646* (2013.01); *B05B 17/0684* (2013.01); *B41J 2/00* (2013.01); *Y10T 137/6416* (2015.04); *Y10T 137/8359* (2015.04); *Y10T 137/85978* (2015.04)

(58) Field of Classification Search
CPC .. B01F 3/04; B01F 3/04007; B01F 3/04085; B05B 17/0646; B05B 17/0684
USPC ....... 261/142, 94, 97, 99, DIG. 65, DIG. 88, 261/DIG. 89
See application file for complete search history.

(56) References Cited

U.S. PATENT DOCUMENTS 5,975,675 A 11/1999 Kim
6,261,347 B1 7/2001 Moreland
(Continued)

FOREIGN PATENT DOCUMENTS

CN 1223637 C 10/2005
JP 2005185366 A 7/2005
(Continued)

OTHER PUBLICATIONS

PCT Search Report dated Jun. 19, 2015; PCT/US2015/036546, 5 Pages.
(Continued)

*Primary Examiner* — Robert A Hopkins
(74) *Attorney, Agent, or Firm* — Abbey A. Lopez; David M. Weirich

(57) ABSTRACT

A microfluidic fluid delivery device and method. The device includes a reservoir and a transport member. The device includes a microfluidic delivery member including a microfluidic die configured to release a fluid composition from the device. The microfluidic delivery member includes an adapter configured to receive an end portion of the transport member, wherein a capillary passage is formed between the adapter and the transport member. The capillary passage has a largest effective pore size that is smaller than the average effective pore size of the transport member.

34 Claims, 16 Drawing Sheets

(56) References Cited

U.S. PATENT DOCUMENTS

| | | |
|---|---|---|
| 6,325,475 B1 | 12/2001 | Hayes et al. |
| 6,371,451 B1 | 4/2002 | Choi |
| 7,367,661 B2 | 5/2008 | Hess et al. |
| 8,020,573 B2 | 9/2011 | Lamers et al. |
| 8,870,090 B2 * | 10/2014 | Feriani ............... B05B 17/0646 239/102.1 |
| 2002/0192255 A1 | 12/2002 | Schiavo et al. |
| 2004/0032468 A1 | 2/2004 | Killmeier et al. |
| 2006/0065755 A1 | 3/2006 | Sugita et al. |
| 2010/0154790 A1 | 6/2010 | Merassi et al. |

FOREIGN PATENT DOCUMENTS

| | | |
|---|---|---|
| JP | 2005224504 A | 8/2005 |
| JP | 2007054446 A | 3/2007 |
| KR | 100238582 B1 | 1/2000 |
| WO | WO 2004/044552 A2 | 5/2004 |
| WO | WO 2014/043424 A1 | 3/2014 |

OTHER PUBLICATIONS

PCT Search Report dated Sep. 17, 2015; PCT/US2015/036549, 11 Pages.
PCT Search Report dated Sep. 18, 2015; PCT/US2015/036551, 9 pages.
U.S. Appl. No. 14/310,285, filed Jun. 20, 2014, Dana Paul Gruenbacher, et al.
U.S. Appl. No. 14/310,311, filed Jun. 20, 2014, Dana Paul Gruenbacher, et al.
U.S. Appl. No. 14/310,334, filed Jun. 20, 2014, Dana Paul Gruenbacher, et al.
U.S. Appl. No. 14/310,367, filed Jun. 20, 2014, Dana Paul Gruenbacher, et al.

* cited by examiner

MICROFLUIDIC DELIVERY SYSTEM FOR RELEASING FLUID COMPOSITIONS

FIELD

The present invention generally relates to a system for delivering a composition into the air or onto a surface. More particularly, the invention relates to microfluidic delivery systems, devices and methods, including delivering fluid compositions such as perfumes, using at least one microfluidic die.

BACKGROUND

Various systems exist to deliver volatile compositions, such as perfume compositions, into the air by energized (i.e. electrically/battery powered) atomization. In addition, recent attempts have been made to deliver scents using microfluidic delivery technology, specifically thermal inkjet technology. However, these attempts are generally directed to printing ink-based scented fluids onto a substrate or surface medium using delivery systems and methods similar to those used for printing ink onto a substrate using thermal inkjet cartridges.

Thermal inkjet technology generally employs a replaceable cartridge that contains fluid ink and a micro-electromechanical ("MEMS") based print head that controls the release of the ink from the cartridge. Generally, the print head includes a die having a plurality of fluid chambers, a heater to heat the ink and a nozzle through which the ink is released onto the substrate. Thermal inkjet cartridges are often designed such that the ink disposed therein is delivered to the die by means of capillary forces that transport the ink in the direction of gravity.

However, when the fluid to be released from the cartridge is to be delivered in a direction at least partially against the force of gravity and/or when the fluid is disposed in the cartridge below the nozzle(s), known wicking and/or gravity-feed configurations may not be suitable. For example, it may be undesirable to use a gravity-feed or typical wicking system if the fluid is to be dispensed upwardly because air bubbles can form in and clog the orifices preventing the fluid composition from being released properly through the nozzle. Moreover, depending on the particular configuration of the device, it may not be possible or desirable to use gravity to feed the die, such as, for example, when the fluid is disposed in the device below the nozzle.

Further, typical ink-jet cartridges are generally opaque and do not allow the user to see the amount of fluid left in the cartridge. This can lead to uncertainty as to when refills need to be changed and/or purchased. Further still, many ink-jet cartridges have very little fluid in the cartridge due to internal structures like sponges within the fluid reservoir. These internal structures can also lead to wasted volume in the reservoir and increased costs.

As such, it would be beneficial to provide a microfluidic delivery device that is configured to reduce the likelihood that air bubbles will obstruct the nozzle. Moreover, it would be beneficial to provide a microfluidic delivery device that is configured to ensure the fluid is available to be released even if the device is configured or oriented such that the nozzle is above the fluid to be released. It would also be desirable to provide a microfluidic delivery device having a fluid transport member that is configured to reduce the likelihood of air bubbles entering the fluid path prior to the nozzle(s). It would also be desirable to have a reservoir that enables the user to see the fluid level left in reservoir. Further, it would be desirable to reduce the amount of non-useable volume in the fluid reservoir.

SUMMARY

In order to provide one or more of the benefits described herein, the present invention may include a microfluidic delivery device comprising a reservoir that forms a hollow body with an opening. The device may comprise a transport member having a first end portion and a second end portion, wherein at least a portion of the first end portion of the transport member is in fluid communication with the reservoir. The first end portion of the transport member has a porous end and/or sides to enable fluid to more from the reservoir through the transport member to the microfluidic delivery device. The device includes an opening in fluid contact with the reservoir. An adapter may be provided for receiving the second end portion of the transport member. A capillary passage is formed at an interface between the wall of the adapter and the second end portion of the transport member. The largest effective pore size of the capillary passage is preferably smaller than the average effective pore size of the first end portion of the transport member. The device may also include a microfluidic delivery member comprising a die wherein the die has a fluid chamber in fluid communication with at least a portion of the second end portion of the transport member at an inlet of the fluid chamber and in fluid communication with a nozzle at an outlet of the fluid chamber.

The present invention may also include a microfluidic delivery device including a reservoir that forms a hollow body with an opening. The device may include a transport member having a first end portion and a second end portion. At least a portion of the first end portion of the transport member is in fluid communication with the reservoir and has a first average effective pore size. The device may also include an opening of the reservoir and an adapter forming a cavity for receiving the second end portion of the transport member. The wall of the adapter compresses the second end portion of the transport member such that the second end portion of the transport member has a second average effective pore size that is smaller than the first average effective pore size. The device preferably further includes a microfluidic delivery member which includes a die having a fluid chamber in fluid communication with at least a portion of the second end portion of the transport member at an inlet of the fluid chamber and in fluid communication with a nozzle at an outlet of the fluid chamber.

The present invention may also include a microfluidic delivery device including a reservoir forming a hollow body with an opening, the hollow body of the reservoir defining a total volume. The device may also include a transport member having a first end portion and a second end portion, wherein at least a portion of the first end portion of the transport member is in fluid communication with the reservoir and a transport member volume. An enclosure at least partly closes the opening of the reservoir forming an aperture and a microfluidic delivery member is disposed adjacent the aperture and including a die. The die has a fluid chamber in fluid communication with at least a portion of the second end portion of the transport member at an inlet of the fluid chamber. The microfluidic delivery member also includes a nozzle at an outlet of the fluid chamber, a filter disposed between the second end of the transport member and the microfluidic delivery member, and a spacer between the filter and the microfluidic delivery member, wherein the spacer provides a gap between the microfluidic delivery member and the filter.

The present invention may also include a microfluidic delivery device comprising a reservoir that forms a hollow body with an opening, wherein the reservoir having a reservoir volume. A transport member having a transport member volume, a first end portion and a second end portion, is provided in fluid communication with the reservoir. An enclosure may at least partly closing the opening of the reservoir. The device may also include a microfluidic delivery member comprising a microfluidic die. The microfluidic die may have a fluid chamber in fluid communication with at least a portion of the second end portion of the transport member at an inlet of the fluid chamber. The microfluidic die preferably also includes a nozzle at an outlet of the fluid chamber. The transport member volume is preferably less than 60% of the reservoir volume.

DETAILED DESCRIPTION

Figure 1:
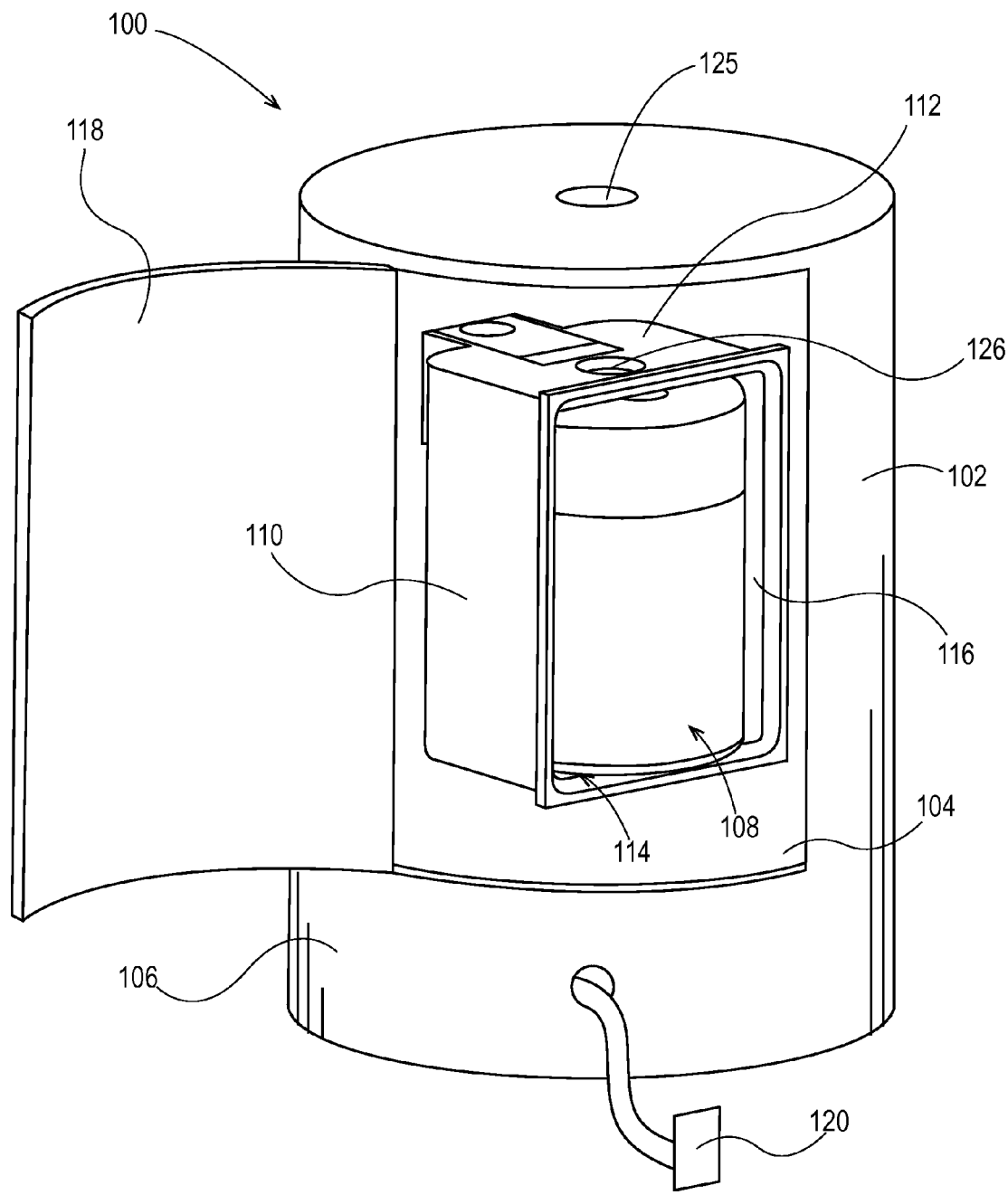
FIG. 1 is a schematic, perspective view of a microfluidic delivery system.

Various non-limiting configurations of the present invention will now be described to provide an overall understanding of the principles of the structure, function, manufacture, and use of the present invention. One or more examples of these non-limiting configurations are illustrated in the accompanying drawings. Those of ordinary skill in the art will understand that the microfluidic delivery systems and methods described herein and illustrated in the accompanying drawings are non-limiting examples and that the scope of the invention is defined solely by the claims. The features illustrated or described in connection with any of the configurations described may be combined with the features of any other configuration and such modifications and variations are intended to be included within the scope of the present disclosure.

The present invention includes a microfluidic delivery system for delivering a composition, for example, into the air, onto a surface, onto a sheet or other pre-formed material, onto the skin, into a receptacle, or to any article, material, or thing. If desired, the microfluidic delivery system may be used to deliver a fluid composition, such as, for example, a perfume composition into the air. Alternatively, or in addition, the microfluidic delivery system may deliver other materials such as enzymes, cosmetic compositions, lotion compositions, cleaning compositions, pigments, ink, light-activated chemistries, cleaning compositions, fabric or surface treating materials, static reducers, allergen reducers, scents, antibacterial agents, anti-viral agents, and/or other desired material or combination of materials. The materials to be delivered by the system can be in the form of fluids, fluids, particles or other solids, gasses, plasma or any other suitable or desired form of material or materials.

The microfluidic delivery system may comprise a housing defining an interior and an exterior. The microfluidic delivery system may be integral within one device or may be separate components permanently or temporarily configured to provide the desired end product. For example, the device may include a decorative housing and a replaceable cartridge disposed therein including some or all of the functional elements of the device. The microfluidic delivery system may also include or be capable of connecting to a power source.

The system may include a reservoir that forms a hollow body with an opening and a transport member disposed in the reservoir. The transport member is intended to allow fluid disposed in the reservoir to move to the nozzles of the device. The transport member preferably has a first end portion and a second end portion separated by a central portion. The first end portion of the transport member is in fluid communication with the reservoir and the first end portion of the transport member is defined by an average effective pore size. The device also includes an adapter having a wall that forms a cavity for receiving the second end portion of the transport member. At the interface of the wall of the adapter and the second end portion of the transport member, a capillary passage is formed. It may be desirable that the capillary passage is smaller in size than the average effective pore size of the first end portion of the transport member in order to help reduce the likelihood that air bubbles will enter the fluid path to the nozzle(s). The adapter may be shaped to match the shape of the transport member. For example, the transport member and the adapter may be cylindrical in shape.

The device preferably includes one or more microfluidic delivery members for delivering the fluid out of the device. For example, the microfluidic delivery member may comprise a microfluidic die. The term "microfluidic die", as used herein means a die comprising a fluid injection system made using a semiconductor micro fabrication process such as thin film deposition, passivation, etching, spinning, sputtering, masking, epitaxy growth, wafer/wafer bonding, micro thin-film lamination, curing, dicing, etc. These processes are known in the art to make MEMs devices. Microfluidic dies may be made from silicon, glass, or a mixture thereof. The microfluidic die comprises a plurality of microfluidic chambers, each comprising a corresponding actuation element: a heating element or an electromechanical actuator. In this way, the microfluidic die's fluid injection system may be micro thermal nucleation (e.g. via heating element) or micro mechanical actuation (e.g. via thin film piezoelectric or ultrasonics). One type of microfluidic die suitable for the microfluidic delivery system of the present invention is an integrated membrane of nozzles obtained via MEMs technology as described in U.S. 2010/0154790, assigned to STMicroelectronics S.R.I., Geneva, Switzerland. In the case of thin film piezo, the piezoelectric material is typically applied via spinning and/or sputtering processes. The semiconductor micro fabrication process allows one to simultaneously make one or thousands of MEMS devices in one batch process (a batch process comprises of multiple mask layers).

The transport member may be defined by a transport member width and the cavity of the adapter may be defined by an adapter width. The adapter width may be smaller than the transport member width (when not compressed) such that the transport member is compressed at the second end portion when disposed in the adapter. As a result once the transport member is wetted, air that may be present in the reservoir will be unable to enter the transport member or the fluid chamber of the die via the capillary passage formed between the wall of the adapter and the second end portion of the transport member. Moreover, as a result of compressing the second end portion of the transport member, the transport member may have a first average effective pore size at the first end portion and a second average effective pore size at the second end portion. It may be desirable that the second average effective pore size is smaller than the first average effective pore size.

The transport member may be designed to provide sufficient fluid composition to the die. For example, the transport member may exhibit an average effective pore size from about 10 microns to about 500 microns, from about 20 microns to about 200 microns, or about 25 microns to about 150 microns.

The transport members may also provide some filtering of particles such that they help reduce the chance that the nozzles become clogged with particles. Thus, it is preferred that the transport member not release or pass particles or other debris that are greater than about half of the diameter of any associated nozzle. In this regard transport members such as fiber wicks may be preferred over, for example, sintered wicks to ensure particles or debris is not passed through the wick.

The reservoir may define a reservoir volume. The transport member, not including the pores contained therein, may be defined by a transport member volume. The transport member volume is preferably less than the reservoir volume to reduce cost of transport member but also to more efficiently dispense a higher percent of the fluid in the reservoir, since there is generally some fluid left in the transport member. It may be desirable that the transport member volume be less than about 60% of the reservoir volume, less than about 40% of the reservoir volume, less than 20% of the reservoir volume, or less than 10% of the reservoir volume. As such, the transport member may be sized to sufficiently supply the die with fluid composition while also allowing sufficient volume of the reservoir available for the fluid composition. Controlling the transport member volume in relation to the reservoir volume allows control of the amount of fluid composition that may be contained within the reservoir. In addition, it may be desirable to make at least a portion of the reservoir clear, transparent or translucent to allow the user to see how much fluid is left in the reservoir. Further, having a transport member that takes up less volume than the typical sponge found in ink jet cartridges can also help make the fluid level more visible to the user.

In simple terms, during use, the fluid composition travels from the reservoir, through the transport member, and into the die. In the die, the fluid composition travels into the fluid chamber and to the nozzle where it is expelled through an orifice into the air or onto the desired surface, etc. Where heat is used to volatilize a portion of the fluid composition, the fluid in the die is heated producing a vapor bubble that causes a droplet of the fluid composition to be released through the orifice in the nozzle.

FIG. 1 is an example of a microfluidic delivery system of the present invention. As shown, the microfluidic delivery system 100 comprises a housing 102 defining an interior 104 and an exterior 106. The housing 102 may comprise a holder member 110 disposed in the interior 104 of the microfluidic delivery system 100. The housing 102 may include a door 118 or other structure for accessing the interior 104. The microfluidic delivery system may also include a power source 120 integral with or extending from the housing. The microfluidic delivery system 100 may be powered by an AC outlet, or may be powered by one or more batteries or other power systems. In battery-powered systems, the battery may be rechargeable, recyclable or disposable.

As shown in FIG. 1, the microfluidic delivery system 100 may includes a cartridge 108 that is releasably connectable with an optional holder member 110, and thus, the housing 102. As shown, the cartridge 108 may be connected with the housing by sliding the cartridge 108 into the holder member 110 such that the cartridge touches the bottom wall 114, side wall(s) 116, and/or top wall 112 of the holder member 110.

The cartridge 108 may be reusable, refillable and/or replaceable depending on the desired use of the system. The cartridge 108 may also include other structure of the system, such as, for example, a wick, a die, electrical contacts and/or a nozzle, which are described in more detail herein. The housing 102 may also include one or more housing apertures 125 to allow the fluid composition to pass out of the cartridge 108 to the exterior 106 of the housing. If used, the holder member 110 may include a holder aperture 126 or other opening that can be aligned with the housing aperture 126 during use.

Figure 2:
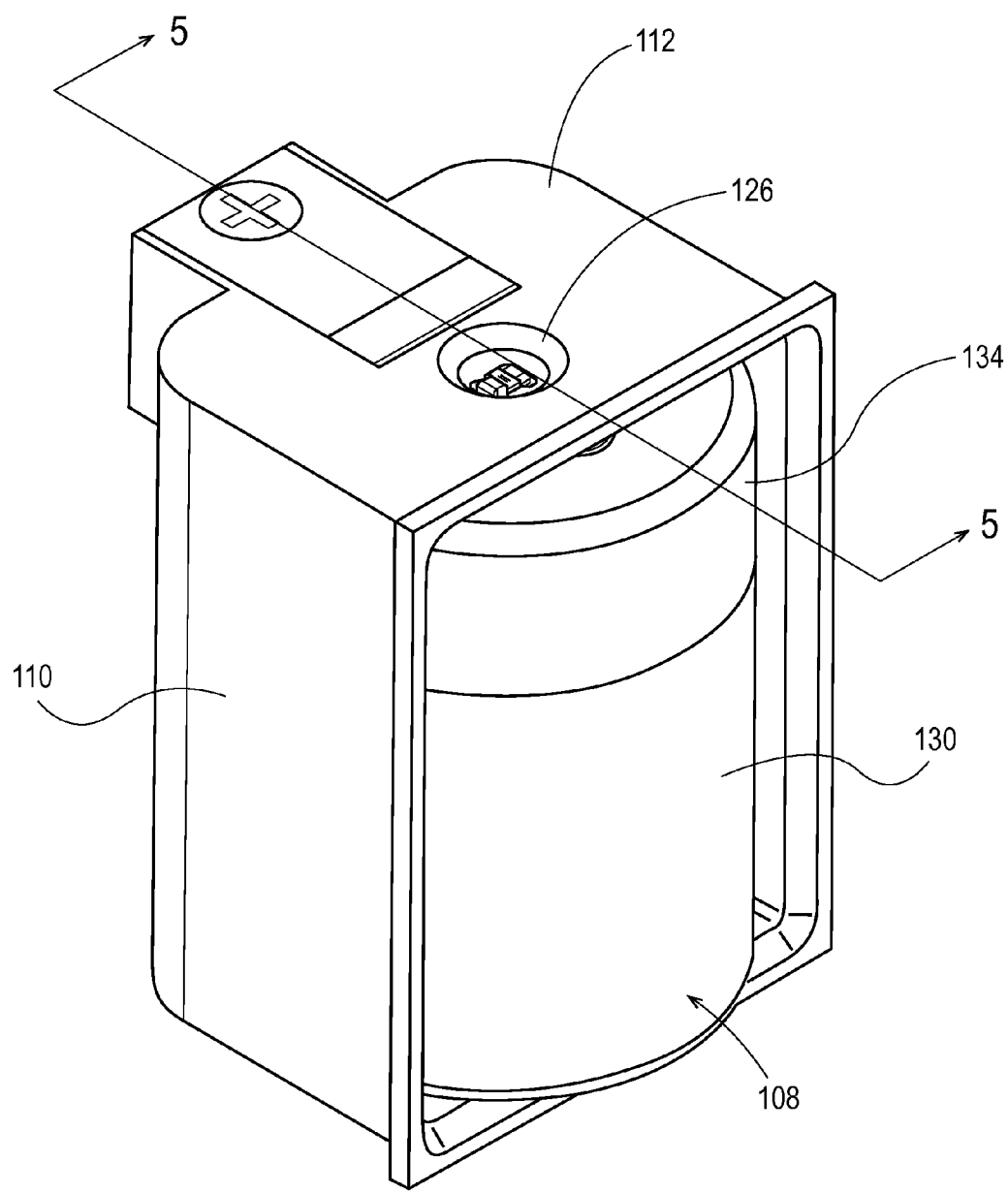
FIG. 2 is a perspective view of a holder member and a cartridge of a microfluidic delivery system, wherein the cartridge is in the holder member.
Figure 3:
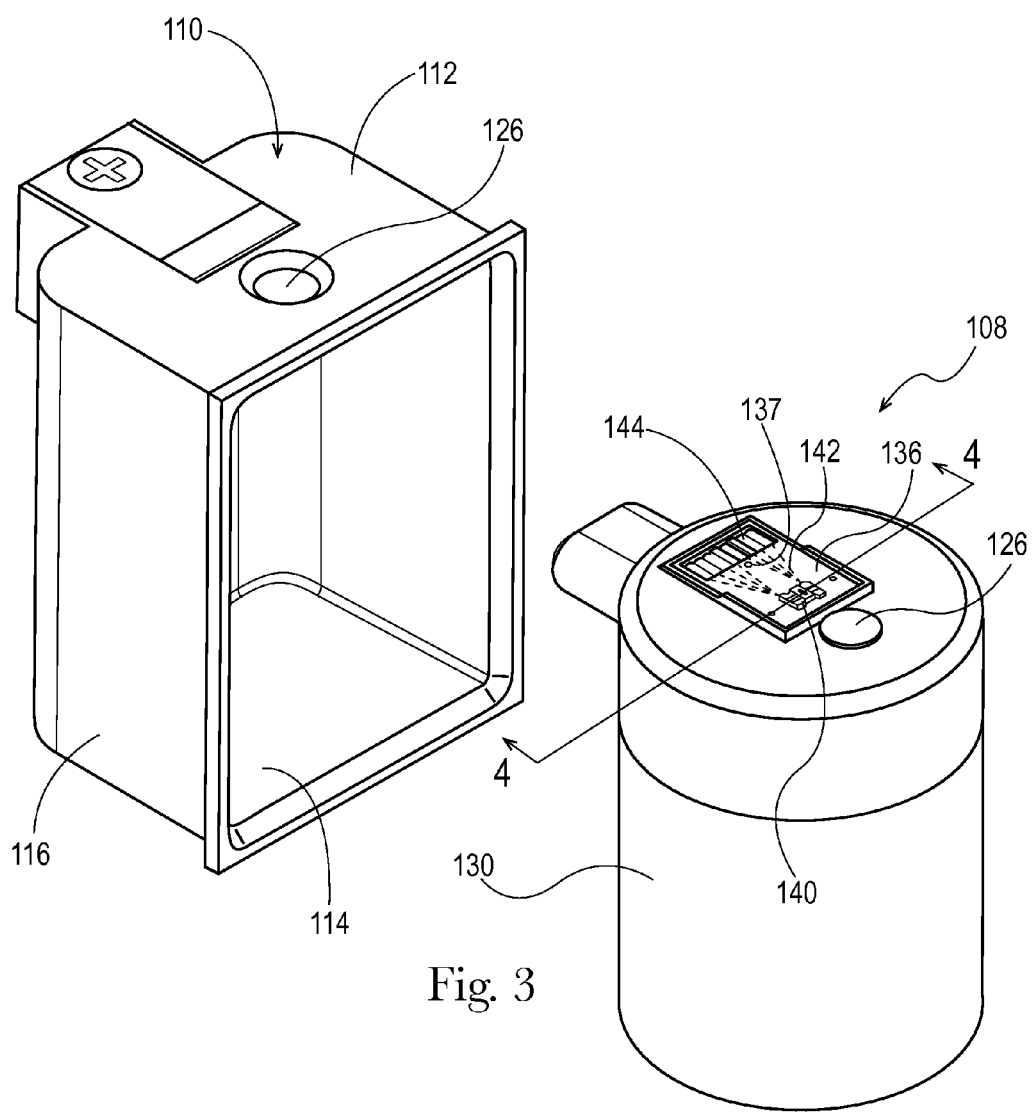
FIG. 3 is a perspective view of a holder member and a cartridge of a microfluidic delivery system, wherein the cartridge is shown out of the holder member.

FIG. 2 shows the cartridge 108 disposed in the holder member 110. FIG. 3 shows the cartridge 108 removed from the holder member 110. The cartridge 108 may be releasably connected with the holder member 110 in any suitable way.

Figure 4:
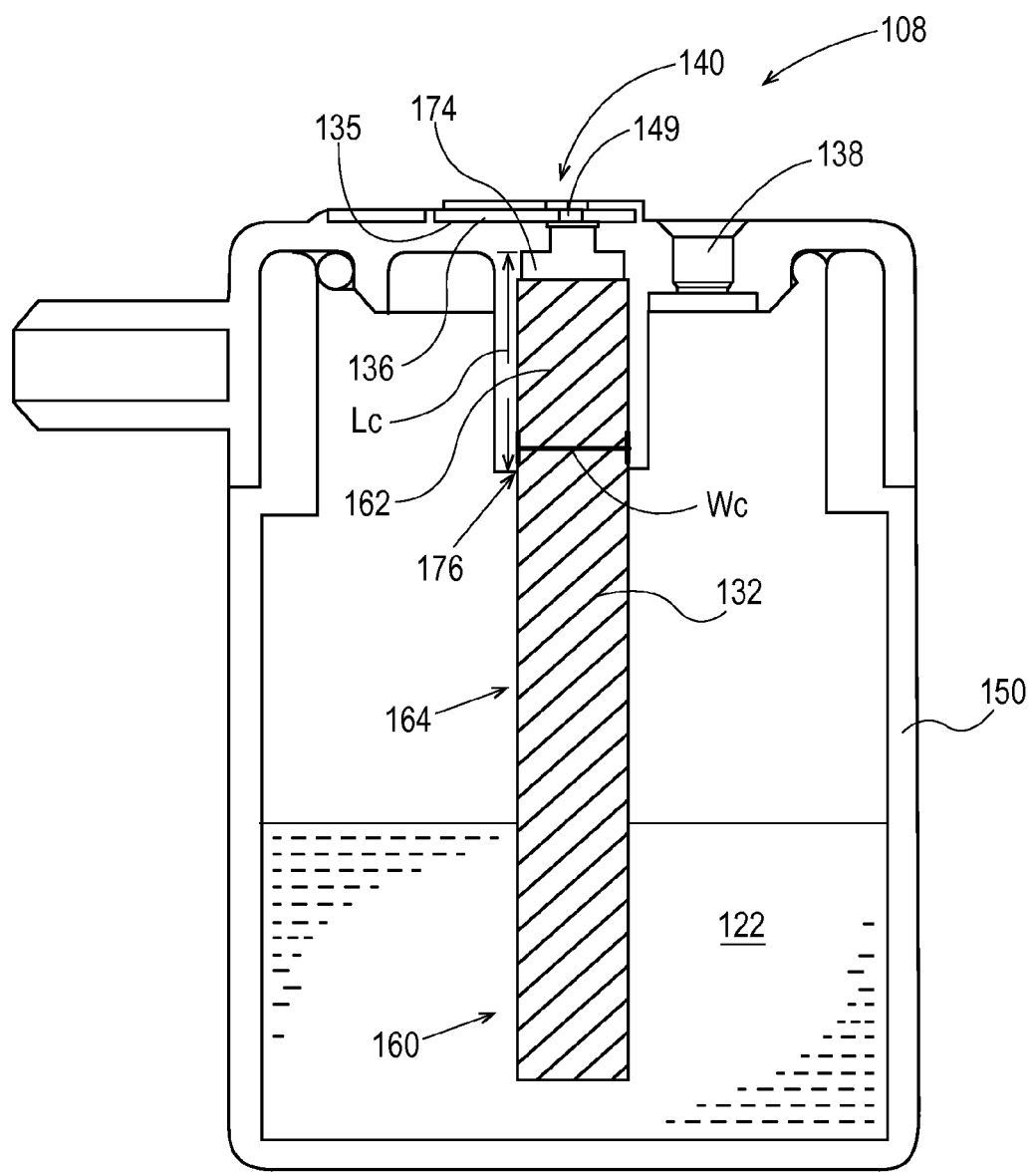
FIG. 4 is a sectional view of the cartridge of FIG. 3 taken along line 4-4.

As shown in FIGS. 2-4, the cartridge 108 includes a reservoir 130 for holding a fluid composition 122, and may include a transport member 132 that is in fluid communication with the reservoir 130. The cartridge 108 may include an optional lid 134 that encloses the reservoir 130. The cartridge 108 may also include a microfluidic delivery member 136 for delivering the fluid composition 122 contained within the reservoir 130 into the air, for example. While it is shown in FIG. 3 that the microfluidic delivery member 136 is disposed on a part of the lid 134, it is to be appreciated that the microfluidic delivery member 136 may be disposed on other portions of the cartridge 108, lid 134, holder member 110 or housing 102. For example, it may be desired that the cartridge 108 is a unitary structure with no lid 134 and that a portion of the cartridge 108 itself includes the microfluidic delivery member 136.

FIGS. 3-6 show the microfluidic delivery member 136 including a die 140 and electrical leads 142. The electrical leads 142 provide electrical communication from the power source 120 to the die 140. The electrical leads 142 are in electrical connection with electrical contacts 144. In the particular embodiment shown, the electrical contacts 144 are disposed at an end portion of the electrical leads 142 most distant from the die 140, although, this particular configuration is not required. The electrical contacts 144 are configured to provide electrical communication with electrical connections of the holder member 110.

Figure 7:
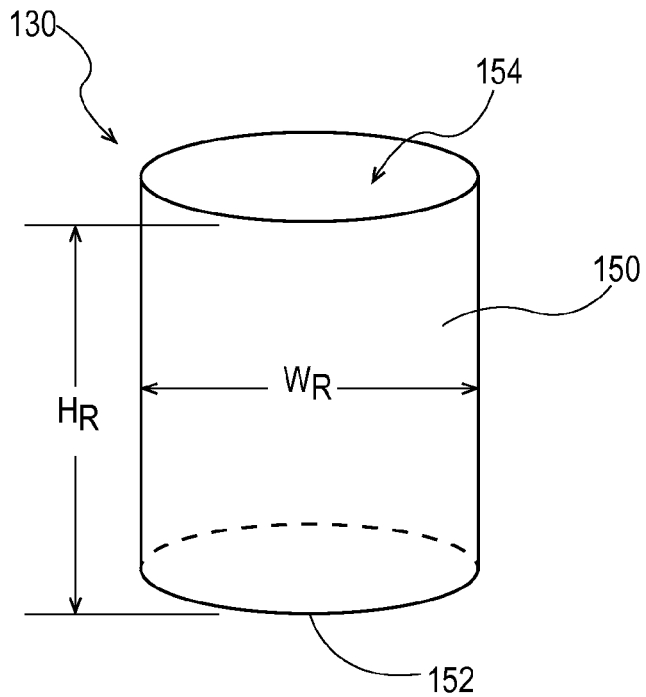
FIG. 7 is a perspective view of a cylindrical-shaped reservoir.
Figure 8:
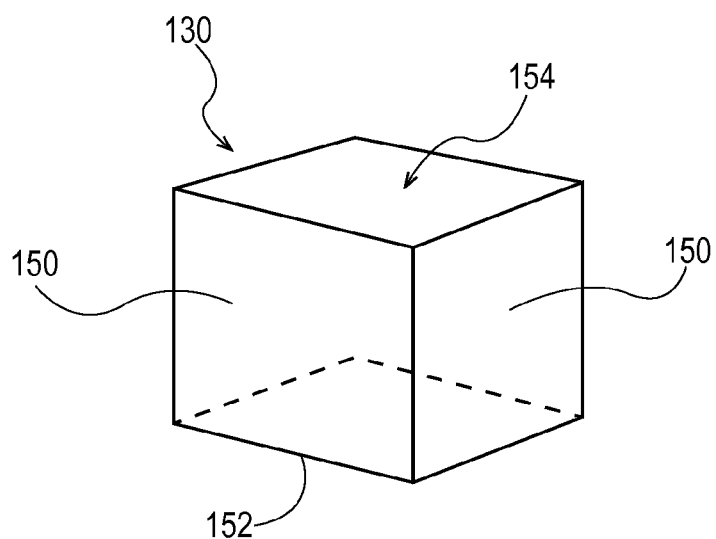
FIG. 8 is a perspective view of a cube-shaped reservoir.

With reference to FIGS. 7 and 8, the reservoir 130 includes a generally hollow body for containing, for example, a fluid composition therein. The reservoir 130 may include one or more adjoining walls 150, a base 152 connected with the walls 150, and an opening 154 opposite the base 152. The reservoir 130 may be configured to be any desired shape or size. For example, the reservoir 130 may have a height $H_R$ of from about 20 mm to about 60 mm, and a width $W_R$ of from about 15 mm to about 40 mm and may have a cylindrical shape, as shown in FIG. 7, or may have a cube-like shape as shown in FIG. 8. The reservoir 130 may be made from any suitable material, including glass, metal or polymeric materials such as, for example, polyester or polypropylene. The reservoir 130 may be transparent, translucent, or opaque, for example. If transparent or translucent, it may provide a way for the user to determine when the refill is used up and needs to be replaced or refilled.

Figure 9:
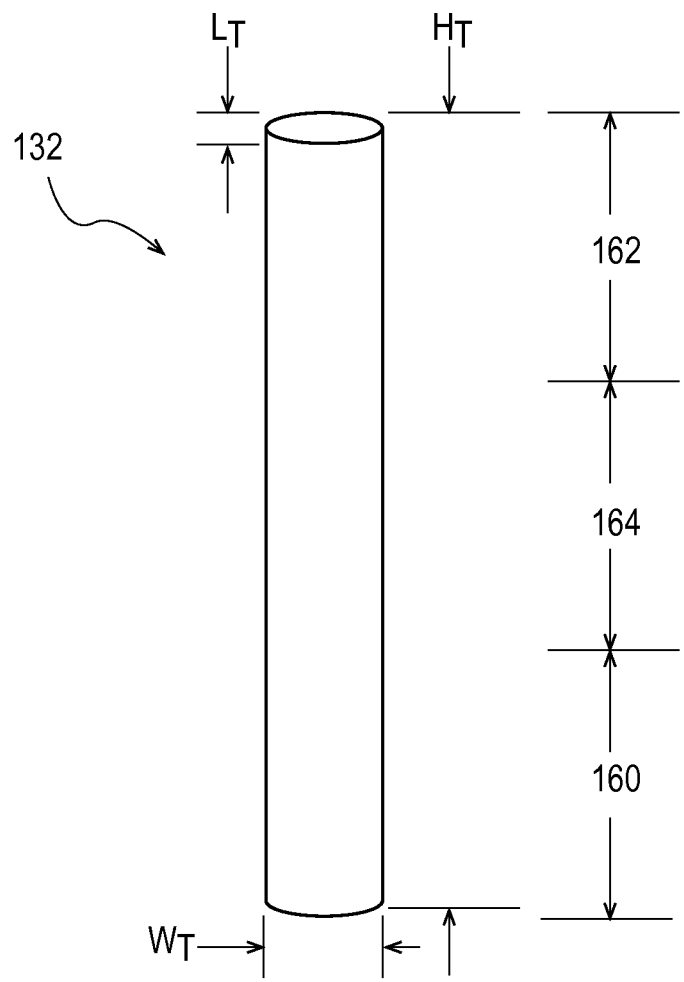
FIG. 9 is a perspective view of a transport member.

With reference to FIGS. 4 and 9, it is shown that the transport member 132 may include a first end portion 160, a second end portion 162, and a central portion 164. For simplification and if not otherwise set forth herein, each of the portions may be considered to comprise approximately ⅓ of the length of the transport member 132, although other configurations are contemplated wherein the transport member 132 has any number of regions with different characteristics. For example, the transport member 132 may have only a first end portion 160 and a second end portion 162 with different characteristics or may include any number of different portions with different characteristics.

The first end portion 160 of the transport member 132 is preferably configured such that at least a portion of it is in fluid communication with the fluid composition 122 at least some time during or before the device is used. The second end portion 162 is preferably configured to at least partially extend out of the fluid composition at least some time during use and may extend out of the reservoir 130. The second end portion 162 may be disposed adjacent the microfluidic delivery member 136. The first end portion 160 may extend all or part of the way to the base 152 of the reservoir 130. In some embodiments, the transport member 132 may be completely surrounded by the walls 150 of the reservoir 130. Depending upon the configuration of the microfluidic delivery system 100, the fluid composition 122 may travel in either direction through the transport member 132. For example, the fluid composition 122 may travel from the first end portion 160 to the second end portion 164 or in the opposite direction. Further, the fluid composition 122 may travel in a direction with or in opposition to gravity. This can be achieved by capillary action, wicking, diffusion, suction, siphon, vacuum, pumping or any other suitable means for moving the fluid through the transport member 132. The transport member 132 may be configured to have any desired shape and length. For example, the transport member 132 may have a generally cylindrical shape as shown in FIG. 9.

The lid 134, if present, may be connected with, and provide an enclosure to, the reservoir 130. The lid 134 may be made from various materials, including a solid polymeric material such as polyester or polypropylene, and may be rigid or flexible, as desired. The lid 134 may connect with the reservoir 130 in any suitable way. For example, the lid 134 may be threaded onto the reservoir 130 or may snap onto the reservoir 130 using one or more fasteners. The lid 134 and the reservoir 130 may be integrally formed, or releasably connectable, permanently connected or semi-permanently connected to each other. One example of a preferred lid 134 is one that has a material that enables a good seal on the surface. For example, the lid 134 may include a compressible material can be a foam, or resilient material that is also chemically compatible with the fluid 122 in the reservoir 130.

Figure 10:
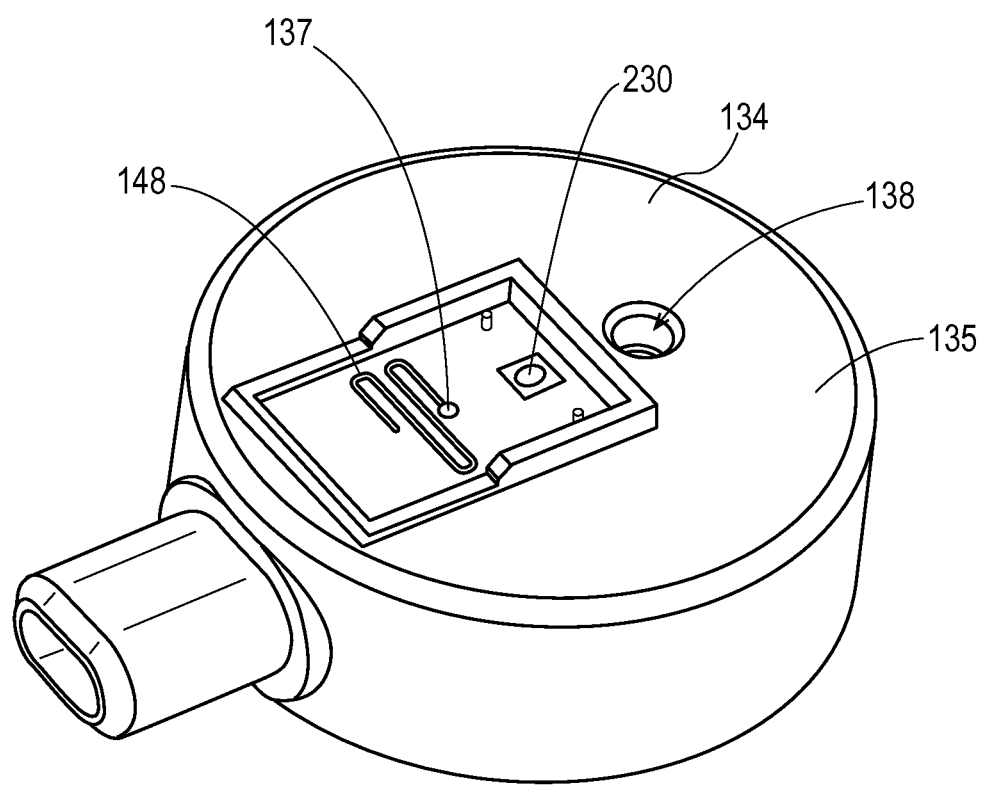
FIG. 10 is a perspective view of a portion of the device of the present invention.

As shown in FIG. 10, the lid 134 may comprise a fill port 138 to allow for filling of the reservoir 130. As such, embodiments are contemplated wherein the cartridge 108 may either be filled when the lid 134 is connected to the reservoir 130 or with the lid 134 removed from the reservoir 130.

As shown in FIG. 10, the lid 134, microfluidic delivery member 136 and/or reservoir 130 may comprise a vent port 137 so that air is able to replace the fluid composition 122 which is released from the cartridge 108. The vent port 137 may be in fluid communication with a vent channel 148 in the lid 134 that directs the air into the reservoir 130 through a vent port 137 (shown in FIG. 3) in the microfluidic delivery member 136. The vents can be configured to allow the air pressure above the fluid 122 in the reservoir 130 can remain at atmospheric pressure as the fluid 122 is discharged from the reservoir 130. This allows the microfluidic delivery member 136 to remain primed and/or prevents or at least reduces back pressure in the fluid path.

The lid 134 or reservoir 130 may include an adapter 170 (shown in FIG. 4) that connects the transport member 132 with the lid 134. The adapter 170 may be integrally formed with the lid 134, as shown in FIG. 3, or the adapter may be a separate component that is connected with an inner surface 139 of the lid 134. The adapter 170 may be made from the same material as the lid 134, or may be made from one or more different materials.

The interface between the adapter 170 and the transport member 132 is an area where air may enter and eventually block the die 140 from releasing the fluid composition 122. At the interface between the adapter 170 and the second end portion 162 of the transport member 132, a capillary passage 176 may be formed. As such, in order to prevent air from entering the transport member 132 along the capillary passage 176, the average effective pore size of the transport member 132 in the first end portion 160 and the central portion 164 should be greater than the average effective pore size of any capillary passage 176 that may be formed at the interface of the adapter 170 and the second end portion 162 of the transport member 132. This can be accomplished, for example, by compressing the second end portion 162 of the transport member 132 at the adapter 170. In addition or alternatively, the transport member 132 may be designed such that it has a smaller average effective pore size at the second end portion 162 than the first end portion 160 while having the average effective pore size of both the first end portion 160 and the second end portion 162 still be larger than the largest effective pore size of the capillary passage 176.

The adapter 170 may comprise one or more walls 172 that form a cavity 174 (shown in FIG. 4) for receiving the transport member 132. The walls 172 of the adapter 170 may be configured to compress all or a portion of the second end portion 162 of the transport member 132 to create an interference fit. The walls 172 of the adapter 170 may completely surround a portion of the second end portion 162 or may only partly surround the second end portion 162. The adapter 170 may be any desired size or shape. For example, the adapter 170 may form a cavity 174 that has a shape that matches the shape of the exterior of the transport member 132. Such a configuration may allow the adapter to provide generally uniform compression forces to the second end portion 162 of the transport member 132, which can help reduce the likelihood of forming a capillary passage 176 at the interface of the adapter 170 and the transport member 132 that is large enough to allow air into the transport member 132.

The cavity 174 may define a width $W_C$ and a length $L_C$, as shown in FIG. 4. The width $W_C$ may be any suitable size, including, for example in the range of from about 3 mm to about 10 mm and the length $L_C$ may be any suitable size, including in the range of from about 5 mm to about 25 mm. The cavity 174 of the adapter 170 may extend in a single direction or may change directions over its length $L_C$. For a tapered cavity, the cavity width Wc is measured at the narrowest cavity width to which the second end portion 162 of the transport member 132 is exposed when the transport member 132 is inserted into the adapter 170 for operation of the microfluidic device.

Figure 5:
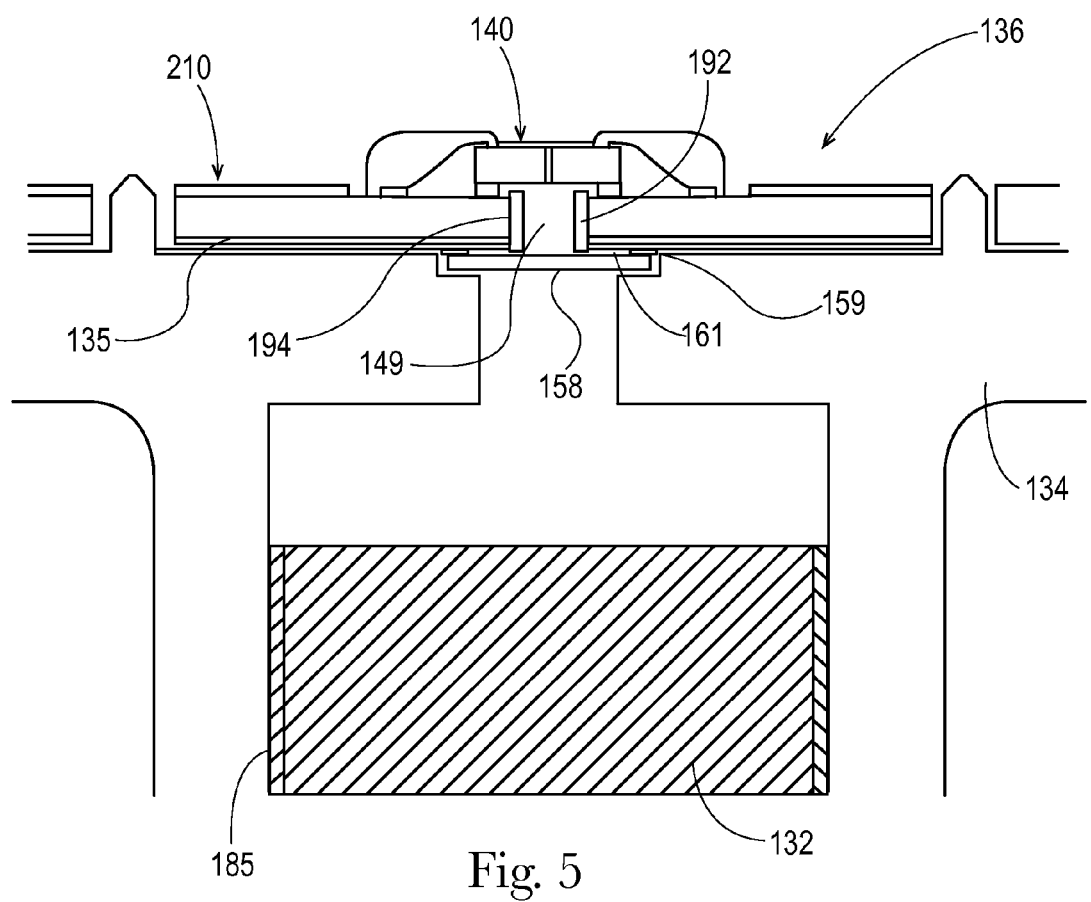
FIG. 5 is a sectional view of the cartridge of FIG. 2 taken along line 5-5.

As shown in FIGS. 4 and 5, the cartridge 108 may include an aperture 149 to provide fluid communication between the transport member 132 and the die 140. The cartridge 108 may also include a filter 158 to prevent particles or other unwanted materials from entering the die 140. The filter 158 may be positioned between the transport member 132 and the die 140. Further, the filter 158 may be attached to the die 140, which may help protect the die 140 from contamination.

The filter 158 may be any suitable filter structure, including, for example, a porous structure having interstitial spaces that allow the fluid composition to pass, but block materials (e.g. particles, fibers, etc.) of a predetermined size from entering the die 140. For example, the filter 158 may block particles that have a dimension greater than about one-half, or about one-third the size of the smallest fluid passage in the die 140. Exemplary nozzles and/or fluid passages may be as small as about 13 to about 25 microns in diameter. In such cases, the filter 158 should filter particles greater than about 10 microns, preferably greater than about 5 microns, preferably greater than about 2 microns.

The filter 158 may be disposed in the cartridge 108 such that the fluid composition 122 may pass from the transport member 132, through the filter 158, through the aperture 149 to the die 140. The filter 158 may be attached to the cartridge 108 or the lid 134 in any suitable way, including friction, adhesive, mechanical fasteners and the like. It is also contemplated that the transport member 132, or any portion thereof, may act as a filter 158, itself, or in addition to any separate filter 158 that may be provided. Exemplary embodiments of filter materials include woven or non-woven mesh materials (e.g. stainless steel, silicon, or polymeric mesh), fibrous structures, foams and particles.

The filter 158 may be separated from the microfluidic delivery member 136 by a mechanical spacer 159. The first mechanical spacer 159 may create a gap 161 between the lower surface 135 of the microfluidic delivery member 136 and the filter 158. In that regard, the area outlet of the filter 158 may be greater than the area of the aperture 149. This design can help reduce the likelihood that the flow of the filter will be reduced below a desired level as it gets clogged up with debris. Preferably, the mechanical spacer 159 is between about 100 and about 700 microns thick.

The mechanical spacer 159 may be a separate rigid support, a protrusion formed on the lower surface 135 of the microfluidic delivery member 136, such as the solder mask, or adhesive material that conforms to a shape that provides an adequate distance between the filter 158 and the lower surface 161 of the microfluidic delivery member 136.

As shown in FIG. 5, the aperture 149 may include a liner 192 that covers exposed sidewalls 194 of the printed circuit board 210. The liner 192 may protect against particles from the printed circuit board 210 from entering into the fluid path and blocking the nozzles 188. For instance, the sidewalls 194 of the aperture 149 may be lined with a material that is less reactive to the fluid in the reservoir than the material of the printed circuit board 210, such as gold or any other suitable material.

Figure 6:
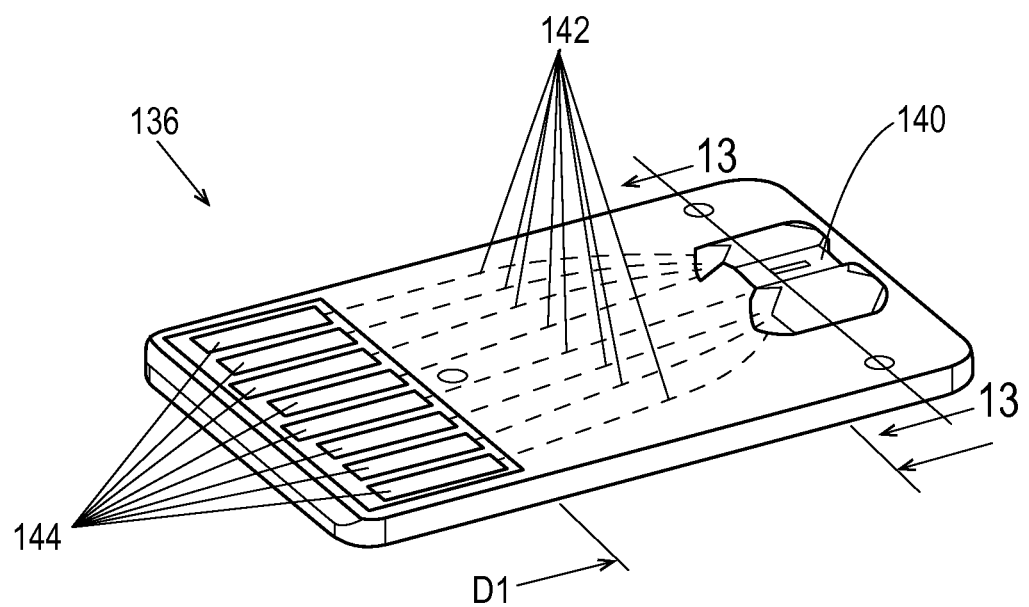
FIG. 6 is a perspective view of a microfluidic delivery member.

As discussed above, the cartridge 108 may include a microfluidic delivery member 136. An example of a microfluidic delivery member 136 is shown in FIGS. 6 and 13. The microfluidic delivery member 136 shown includes a die 140 and electrical leads 142 connected with the die 140. As shown in FIGS. 12, 12A, 16 and 17, the die 140 comprises one or more fluid channel 156 that are in fluid communication with one or more fluid chambers 180. Each fluid chamber 180 has one or more adjoining walls 182, an inlet 184, and an outlet 186. The inlet 184 of each fluid chamber 180 is in fluid communication with one of the fluid channels 156 of the die 140 and the outlet 186 of each fluid chamber 180 is in fluid communication with an orifice 190 of a nozzle 188. The fluid chambers 180 may be configured to have any desired shape or size.

Figure 11:
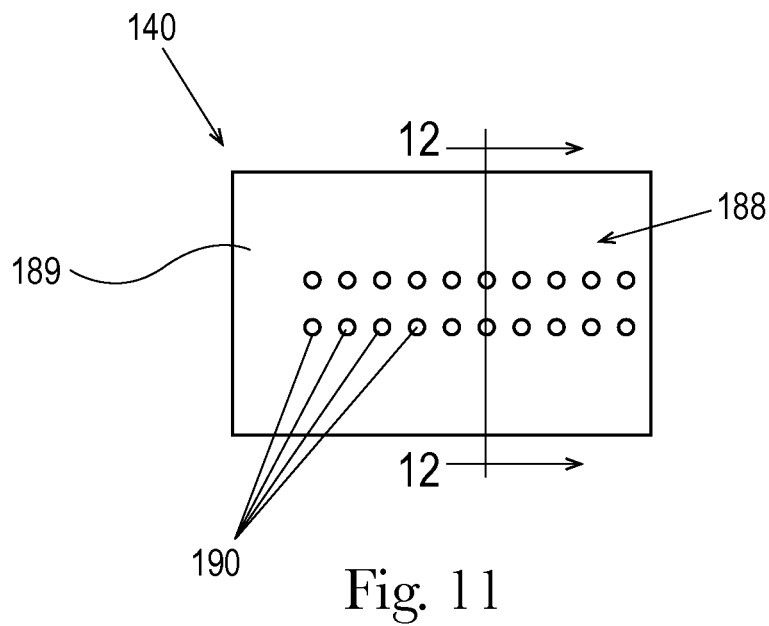
FIG. 11 is a schematic top, plan view of die of a microfluidic delivery member.
Figure 12:
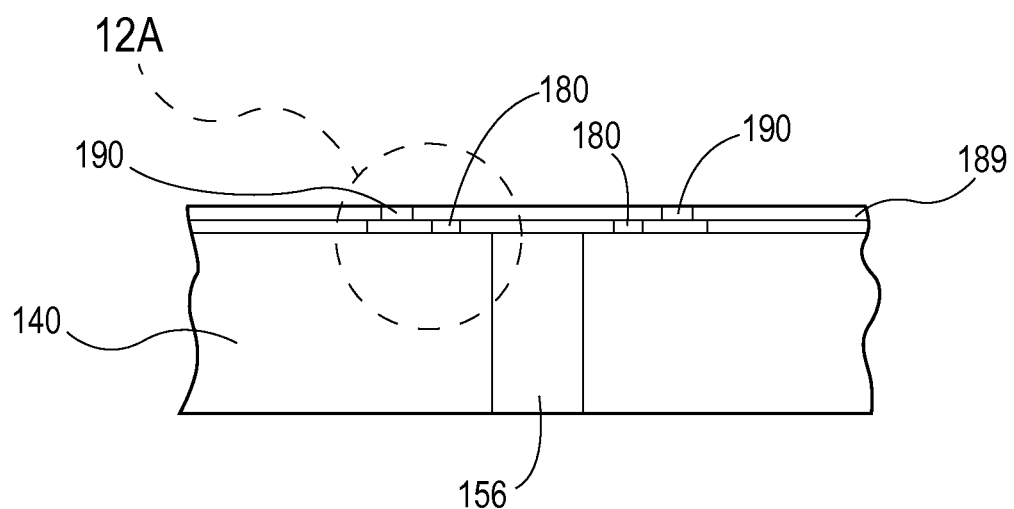
FIG. 12 is a sectional view of the die of FIG. 11 taken along line 12-12.
Figure 12A:
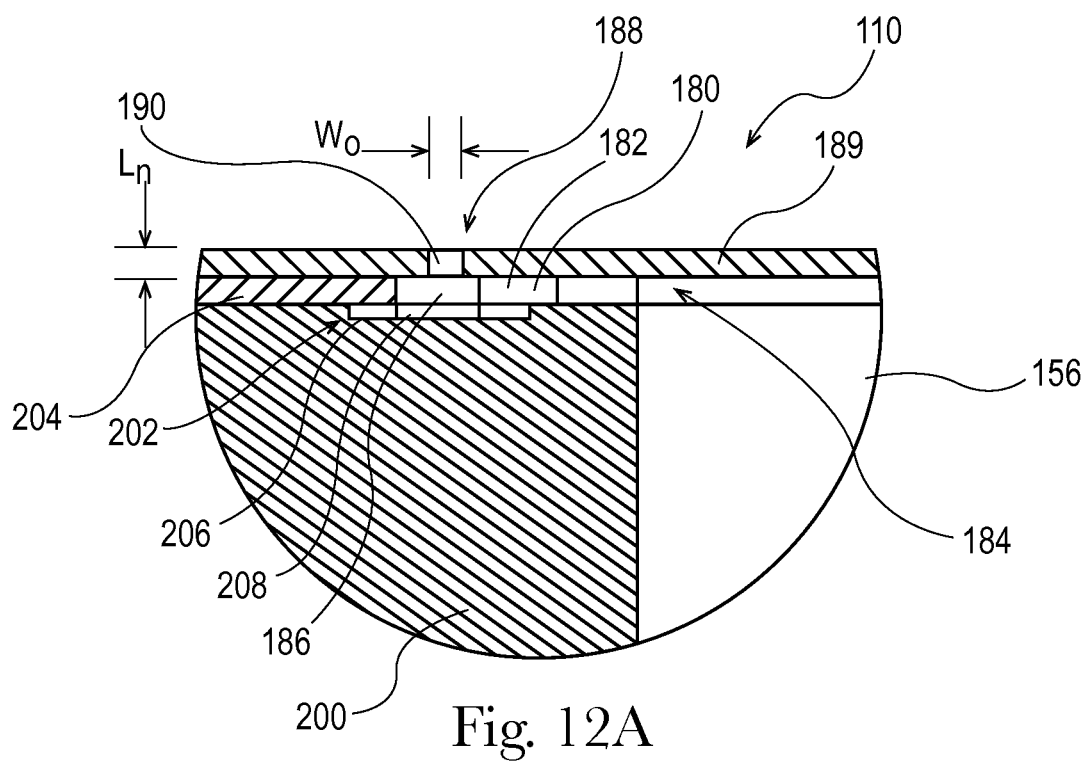
FIG. 12A is a detailed view of portion 12A of FIG. 12.
Figure 13:
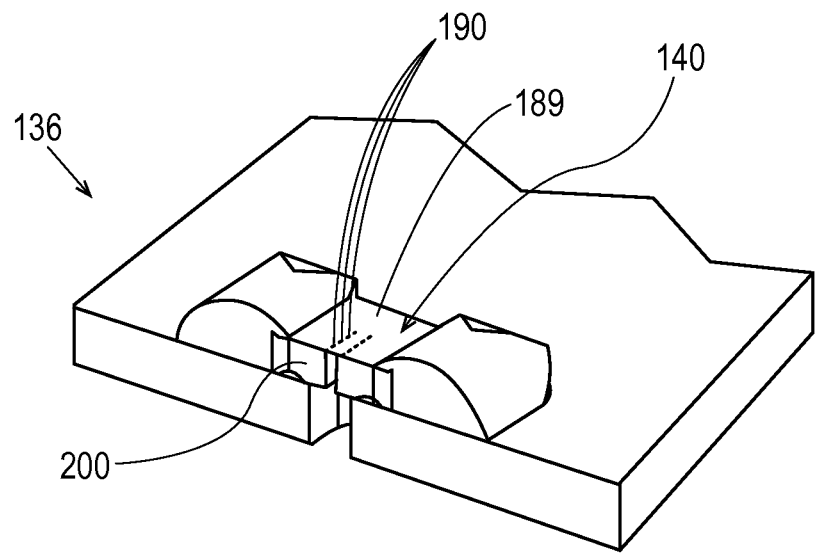
FIG. 13 is a sectional view of the microfluidic delivery member of FIG. 6 taken along line 13-13.

As shown in FIGS. 11, 12 and 12A, the die 140 also includes a nozzle plate 189 having one or more orifices 190. In the embodiment shown, each orifice 190 is in fluid communication with the outlet 186 of a single fluid chamber 180 such that the fluid composition travels from the fluid chamber 180, through the orifice 190 of the nozzle 188 in fluid communication with the fluid chamber 180, and into the air.

The nozzle plate 189 may be configured in various different ways. For example, the nozzle plate 189 may have a thickness $L_N$ of about 10 microns to about 30 microns, or about 20 microns to about 30 microns. The nozzle plate 189 may be composed of any suitable material. Exemplary materials include dry photoresist material such as TMMF, available from Tokyo Ohka Kogyo Co, Ltd of Japan, TMMR, SU-8, and AZ4562. The nozzle plate 189 may include any desired number of nozzles and orifices. For example, the nozzle plate 189 may include at least 5 orifices, at least 10 orifices, at least 20 orifices, or from about 5 to about 30 orifices. The orifices 190 may be configured to have any desired shape or shapes. For example, any one or more of the orifices 190 may be generally round, square, triangular, truncated cone-shaped, or oval. The orifices 190 may be configured to have any desired width $W_O$. For example, the width $W_O$ may be in the range of about 15 microns to about 30 microns. The geometry of the fluid chamber 180 and nozzle 188 may be chosen to define the geometry of a drop of fluid composition 122 that is released from the cartridge 108.

Figure 18:
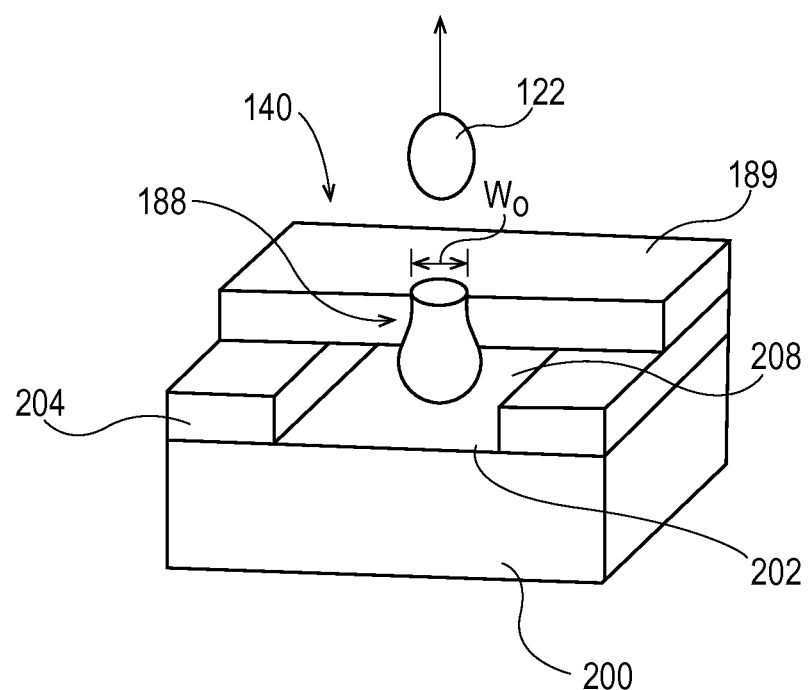
FIG. 18 is a detailed view of portion 18 of the die of FIG. 17.

As shown in FIGS. 12A and 18, the die 140 may include a support substrate 200, conductive layers 202, and one or more polymer layers 204 that define the walls 182 of the fluid chamber 180. The support substrate 200 provides a supporting structure to the conductive layer 202 and polymer layer 204, and defines the inlet 184 of the fluid chamber 180. The support substrate 200 may be made from any suitable material, such as, for example, silicon or glass. The conductive layers 202 are disposed on the support substrate 200, forming electrical traces 206 with relatively high conductivity and heaters 208 with lower conductivity. Other semi-conductive, conductive, and insulative materials may be deposited to form switching circuits or to otherwise provide a means to control electrical signals sent through the electrical traces 206. A heater 208 may be associated with one or more, or each fluid chamber 180 of the die 140. In addition or alternatively, an electro-mechanical element (e.g. piezo element) may be associated with one or more of each fluid chamber 180 of the die 140. The polymer layers 204 may be disposed on the conductive layers 202 and define the walls 182 of the fluid chamber 180 and the outlet 186 of the fluid chamber 180. The nozzle plate 189 of the die 140 is shown in FIG. 12 to be disposed on the polymer layers 204, but other embodiments are contemplated wherein the nozzle 188 is disposed on other layers or materials or is formed from the polymer layers 204, conductive layers 202 or both.

In some exemplary configurations, the microfluidic delivery member 136, including the die 140 and electrical components, is configured as a separate component that is connected to the lid 134, the reservoir, the cartridge, the holding member 110 or the housing member 102. In one exemplary configuration, as shown in FIG. 3, the microfluidic delivery member 136 may take the form of a printed circuit board 210. The printed circuit board 210 may be a rigid or flexible structure. Non-limiting examples of microfluidic delivery members suitable for use in the present invention are described in more detail in U.S. Patent Application titled "MICROFLUIDIC DELIVERY SYSTEM", application Ser. No. 14/310,311, filed on Jun. 20, 2014.

Figure 14:
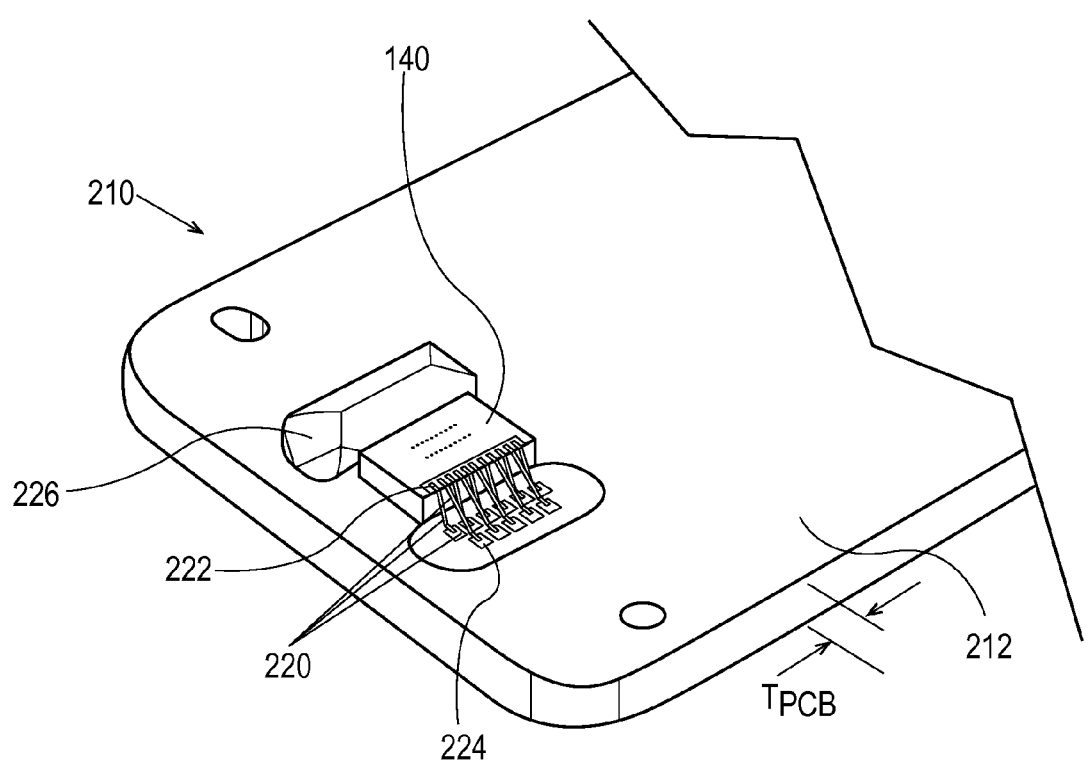
FIG. 14 is a perspective view of a printed circuit board, having portions removed to show details of the electrical connections.

The printed circuit board 210 may include a base substrate 212, as shown in FIG. 14. The base substrate 212 may be any suitable material, including, but not limited to, a rigid material such as a fiberglass-epoxy composite substrate material. The printed circuit board 210 may also include conductive layers on top and/or bottom surfaces of the printer circuit board 210. The conductive layers may include the electrical leads 142 and electrical contacts 144 and may be composed of a metal material such as, for example, copper, silver, or gold.

As discussed above, the microfluidic delivery member, in this case, a printed circuit board 210, may include a vent port 137 that is in fluid communication with the reservoir 130 to allow pressure in the reservoir 130 to equalize as fluid 122 is removed therefrom. That is, as fluid exits the microfluidic delivery member 136 through the nozzles 188, air from the external environment fills the space in the reservoir 130 that is made by the removed fluid.

FIG. 14 shows the die 140 attached to the printed circuit board 210. The die 140 may be attached to any underlying structure by means of an adhesive, such as an epoxy adhesive, or by any suitable attachment means. Further, the electrical connection from the die 140 to the printed circuit board 210 may be established, for example, by a wire bonding process, where small wires 220 are thermally attached to bond pads 222 on the die 140 and to corresponding bond pads 224 on the printed circuit board 210. The small wires 220 may be composed of gold, aluminum or any other suitable material, for example. An encapsulating material 226, such as an epoxy compound, may be applied to the bonded areas between the wires 220 and the bond pads 222 and 224 to protect the delicate connections from mechanical damage and other environmental effects. Bond pads 222 and 224, the conductive paths may be protected by an inert metal coating such as gold, although other materials can be used, such as, for example, tin, silver, or other low reactivity, high conductivity metals.

An inert metal coating in the fluid paths can help protect the printed circuit board 210 from damage caused by the fluid composition 122. In some circumstances, the fluid composition 122 may cause degradation of the materials in the printed circuit board 210 if an inert metal coating or other suitable coating is not used. Further, since the base substrate 212 could be susceptible to migration of the fluid composition 122, the inert metal or other suitable coating may be used to help the fluid paths contain the fluid composition 122 therein.

As shown in FIG. 14, the printed circuit board 210 has a thickness $T_{PCB}$. The printed circuit board 210 may have any desired thickness $T_{PCB}$. For example, the printed circuit board thickness $T_{PCB}$ may be between about 0.5 mm and about 2 mm thick, or between about 0.8 mm and about 1.6 mm thick. Printed circuit boards 210 may have conductive layers on one or both sides, or the printed circuit board 210 can be constructed any desired number of layers. In printed circuit boards 210, connectivity between conductive layers is generally achieved by holes or slots which have been clad in metal through an electroplating process. Such holes or slots are often termed vias. As noted above, the printed circuit board 210 may include aperture 149 located under the die 140.

Figure 15:
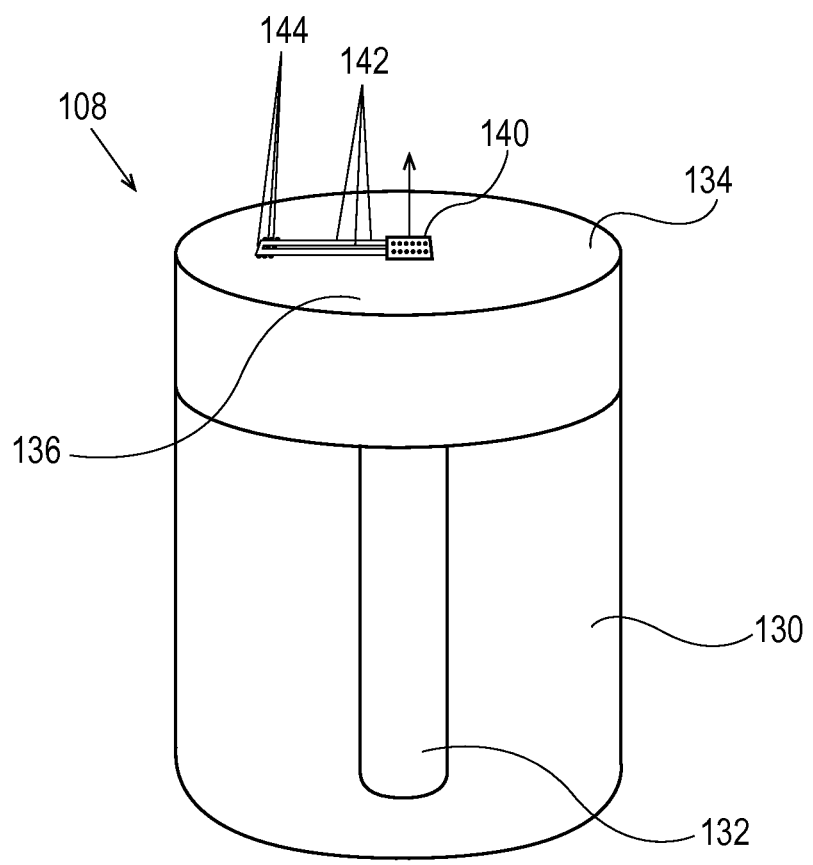
FIG. 15 is a perspective view of a device having a microfluidic delivery member integral with a lid of the device.
Figure 16:
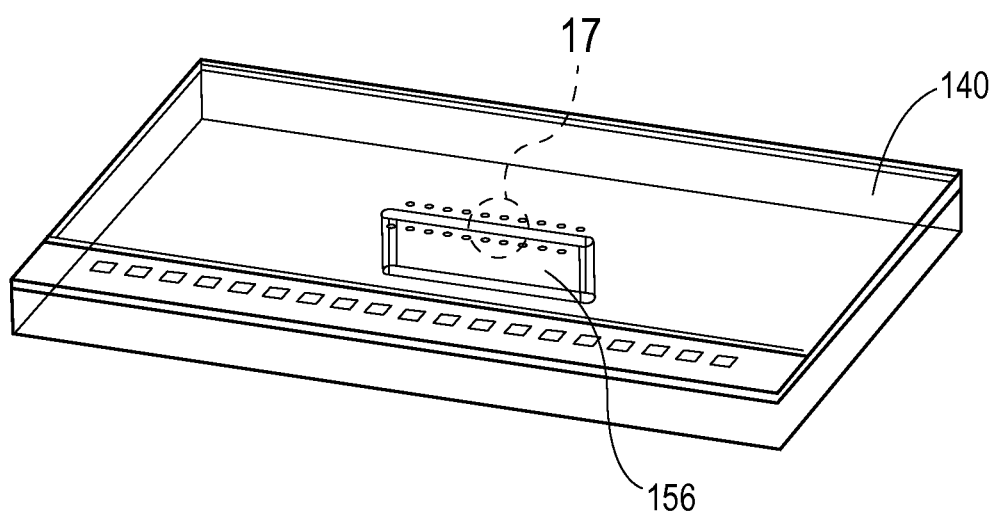
FIG. 16 is a perspective view of a die.
Figure 17:
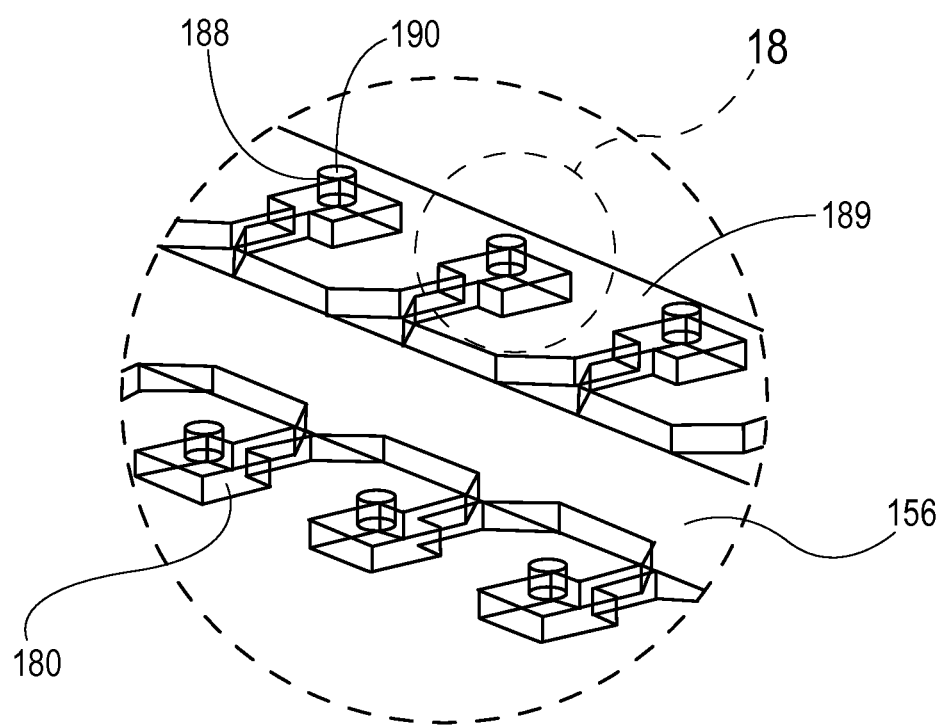
FIG. 17 is a detailed view of portion 17 of the die of FIG. 16.

As shown in FIG. 15, the microfluidic delivery member 136 may be integrally formed with the lid 134 or other portion of the cartridge 108. Technologies such as molded interconnect device (MID) or printing of conductive ink can be used to form the microfluidic delivery member 136. In such configurations, the die 140, electrical leads 142, and electrical contacts 144 can be integrally formed with the lid 134 or other portion of the cartridge 108, instead of being a separate component attached thereto. Thus, the material of the lid 134 or other portion of the cartridge 108 can helps to provide support for a strong electrical connection between the cartridge 108 and the holder member 110.

With reference to FIGS. 4 and 5, the fluid composition 122 travels in a fluid path from the reservoir 130, through the transport member 132, through the filter 158, through the aperture 149 in the lid 134, into the die 140, and is released into the air. The cartridge 108 functions by balancing capillary effects in the die 140 and the transport member 132. Generally, it is preferred that the die 140 is configured such that the highest capillary pressures are within the intended path of the fluid. It is also generally preferred that the transport member 132 is configured to have a lower capillary pressure than the die 140 such that the fluid composition 122 preferentially flows from the transport member 132 into the die 140. The transport member 132 may be selected to have a relatively small porosity and high capillary pressure to aid in the process of priming the cartridge 108, as will be discussed in more detail below. However, in order to maintain priming of the cartridge 108, it is to be appreciated that the gauge pressure of the fluid composition (with respect to the surroundings) at the die 140 and at the transport member 132, taking into account the highest hydrostatic column pressure from the die 140 to the free surface of the fluid composition, should not be less than the maximum capillary pressure capable of being sustained at fluid chambers 180.

The transport member 132 preferably provides a fluid pressure at the die 140 that is slightly below atmospheric pressure. The reduction in fluid pressure at the die 140 below atmospheric pressure created by the hydrostatic column of fluid composition 122 measured from the interface of the transport member 132 and the die 140 to the free surface of the fluid composition 122 into which the transport member 132 is immersed. Having the fluid composition within the die 140 slightly below atmospheric pressure helps prevent the fluid composition 122 from flowing out of the orifices 190 under the influence of hydrostatic pressure or interfacial wetting.

The transport member 132 should be sized such that it provides enough fluid composition to the die 140 under transient conditions. When the microfluidic delivery member 136 causes a droplet of fluid composition 122 to release from the cartridge 108, the capillary forces acting on the fluid composition 122 at the die 140 cause the fluid composition 122 to refill the fluid chamber 180 of the die 140, resulting in an intense, but very short, negative pressure pulse at the second end portion 162 of the transport member 132 that is closest to the die 140. The sufficiency of the transport member 132 to deliver fluid to the fluid chamber 180 of the die 140 is related to the fluid capacity of the transport member 132 and the surface area of the transport member 132 that is exposed to atmosphere. If the fluid capacity of the transport member 132 is too small, or if the surface area of the transport member 132 exposed to atmosphere is too small, the transport member 132 may ingest air and the air can eventually cause de-priming of the microfluidic delivery member 180.

In addition to the short pressure pulses, the transport member 132 may be configured to supply fluid composition 122 to the die 140 at longer time scales related to the user-selected flow rate, for example, when the die 140 is operated continuously. If the resistance to flow of the transport member 132 is too high for the fluid composition 122, then air may be ingested either into the transport member 132 or the die 140, causing de-priming of the microfluidic delivery member 180.

As an estimate of the sufficiency of the transport member 132 to supply fluid composition 122 to the die 140, the maximum resistance to flow may be calculated. If the maximum capillary pressure that can be created by the die 140 is $\Delta p_{max}$, and the required flow rate is n·dV·f, where dV is the drop volume and f is the firing frequency and n is the number of orifices 190, then the resistance to flow can be expressed as:

$$R = \frac{\Delta p_{max}}{n \cdot dV \cdot f}.$$

The transport member 132 may be defined by a height $H_T$, a length $L_T$, and a width $W_T$. For example, the height $H_T$ of the transport member 132 may be in the range of about 1 mm to about 100 mm, or from about 5 mm to about 75 mm, or from about 10 mm to about 50 mm. The length $L_T$ of the transport member 132 may be in the range of about 15 mm to about 55 mm. The width $W_T$ of the transport member 132 may be in the range of about 3 mm to about 10 mm. Further, the width $W_T$ of the transport member 132 may be greater than the width $W_e$ of the cavity. As a result, the adapter 170 may be configured to compress the transport member 132 at the second end portion 162 to prevent air that may be in the reservoir 130 from entering the transport member 132.

In exemplary configurations where capillary transport is used to deliver fluid composition to the die 140, the portions of the transport member 132 may exhibit an average effective pore size. The transport member 132 may exhibit an average effective pore size from about 10 microns to about 500 microns, alternatively from about 20 microns to about 200 microns, alternatively about 25 to about 150 microns. The first end portion 160 and the central portion 164 of the transport member 132 may have a first average effective pore size and the second end portion 162 of the transport member 132 may have a second average effective pore size, wherein the second average effective pore size may be smaller than the first average effective pore size. Alternatively, the first end portion 160 may have a first average effective pore size, the second end portion 162 may have a second average effective pore size and the central portion 164 may have a third average effective pore size. For effective pore size measurements of the first end portion 62, second end portion 162 and central portion 164 of the transport member 132, the transport member 132 is divided into three portions of approximately equal length, a first end portion 160, a central portion 164 and a second end portion 162, and the average effective pore size is measured for each portion. If the transport member 132 has a different number of regions with distinct average effective pore size (e.g. 2 or more than 3), the distinct portions may be measured separately to provide a measurement for each distinct portion. For the average effective pore size of the entire transport member 132, the measurement is taken of the whole, intact, transport member 132.

The volume of the material of the transport member 132, not including the volume of the pores or other open spaces therein, defines a volume of the transport member 132. The volume of the transport member 132 may be configured to take up less than about 60%, less than about 40%, less than about 20%, or less than about 10% of the total volume of the reservoir 130. Keeping the volume of the transport member low increases the amount of fluid composition 122 that may be contained within the reservoir 130 and can help make the fluid level visible if a transparent or translucent reservoir or portion thereof is provided.

The pore volume distribution may also be helpful in characterizing the porosity of the transport member and describing preferred embodiments. For example, it has been found that a transport member 132 with a pore volume distribution having a receding pore volume wherein at least about 80% of the total volume is in pores having radii less than about 150 um, and preferably at least 80% of the total volume is in pores having radii less than about 100 um are preferred. The pore volume distribution is calculated using measurements from the Cumulative Pore Volume Test Method described below.

Cumulative Pore Volume Test Method

This test method is to be conducted on samples that have been conditioned at a temperature of 23° C.±2.0° C. for a minimum of 12 hours prior to the test. All tests should be conducted under the same environmental conditions and in such a conditioned room. First, obtain and inspect the samples to be tested and discard any damaged product. Do not test samples that have defects such as wrinkles, tears, holes, and like. All instruments should be calibrated according to manufacturer's specifications. Samples conditioned as described herein are considered dry samples (such as "dry fibrous wicks or sintered wicks") for purposes of this method. At least four samples are measured for any given material being tested, and the results from those four replicates are averaged to give the final reported value.

Pore volume measurements are made on a TRI/Autoporosimeter (Textile Research Institute (TRI)/Princeton Inc. of Princeton, N.J., U.S.A.). The TRI/Autoporosimeter is an automated computer-controlled instrument for measuring pore volume distributions in porous materials (e.g., the volumes of different size pores within the range from 1 to 1000 µm effective pore radii). Computer programs such as Automated Instrument Software Releases 2000.1 or 2003.1/ 2005.1; or Data Treatment Software Release 2000.1 (available from TRI Princeton Inc.), and spreadsheet programs are used to capture and analyze the measured data. More information on the TRI/Autoporosimeter, its operation and data treatments can be found in the paper: "Liquid Porosimetry: New Methodology and Applications" by B. Miller and I. Tyomkin published in The Journal of Colloid and Interface Science (1994), volume 162, pages 163-170, incorporated here by reference.

As used in this application, porosimetry involves recording the increment of fluid that enters or leaves a porous material as the surrounding air pressure changes. A sample in the test chamber is exposed to precisely controlled changes in air pressure. As the air pressure increases or decreases, different size pore groups drain or absorb fluid. Pore-size distribution or pore volume distribution can further be determined as the distribution of the volume of uptake of each pore-size group, as measured by the instrument at the corresponding pressure. The pore volume of each group is equal to this amount of fluid, as measured by the instrument at the corresponding air pressure. Total cumulative fluid uptake is determined as the total cumulative volume of fluid absorbed. The effective radius of a pore is related to the pressure differential by the relationship:

Pressure differential=[(2)γ cos Θ]/effective radius where γ=fluid surface tension, and Θ=contact angle.

This method uses the above equation to calculate effective pore radii based on the constants and equipment controlled pressures. This in turn also enables us to determine the effective pore size and distribution of pore size within the transport member.

The automated equipment operates by changing the test chamber air pressure in user-specified increments, either by decreasing pressure (increasing pore size) to absorb fluid, or increasing pressure (decreasing pore size) to drain fluid. The fluid volume absorbed or drained at each pressure increment is the cumulative volume for the group of all pores between the preceding pressure setting and the current setting. The TRI/Autoporosimeter reports the pore volume contribution to the total pore volume of the specimen, and also reports the volume and weight at given pressures and effective radii. Pressure-volume curves can be constructed directly from these data and the curves are also commonly used to describe or characterize the porous media.

For this method, the fluid used is a 0.1 weight % solution of octylphenoxy polyethoxy ethanol (Triton X-100 from Union Carbide Chemical and Plastics Co. of Danbury, Conn.) in 99.8 weight % distilled water (specific gravity of solution is about 1.0). The instrument calculation constants are as follows: ρ (density)=1 g/cm³; γ (surface tension)=30 dynes/cm; cos Θ=1. A 1.2 µm Millipore Mixed Cellulose Esters Membrane (Millipore Corporation of Bedford, Mass.; Catalog # RAWP09025) is employed on the test chamber's porous plate. A blank condition (no sample) is run to account for any surface and/or edge effects within the test chamber. Any pore volume measured for this blank run is subtracted from the applicable pore grouping of the test sample.

The sequence of pore sizes (pressures) for this application is as follows (effective pore radius in µm): 10, 20, 30, 40, 50, 60, 70, 80, 90, 100, 120, 140, 160, 180, 200, 220, 240, 260, 280, 300, 350, 400, 450, 500, 550, 600, 650, 700, 750, 800. These pressure values are used to produce the Advancing 1 and Receding 1 curves. This sequence starts with the sample dry, saturates it as the pressure decreases (i.e., Advancing 1 curve), and then subsequently drains the fluid out as the pressure increases again (i.e., Receding 1 curve).

The TRI/Autoporosimeter measures the cumulative weight (mg) of fluid at each pressure level, and reports the respective cumulative pore volume of the sample. From these data and the weight of the original dry sample, the ratio of cumulative pore volume/sample weight can be calculated at any measured pressure level, and reported in mm³/mg. The method used herein helps calculate the effective pore radii based on the constants and equipment controlled pressures. This in turn also enables us to determine the effective pore volume distribution within the transport member. The cumulative pore volume is determined during the Advancing and Receding curves. The average effective pore size of the sample can be calculated using a weighted average of the effective pore radius using the Receding curve volume distribution for each pore radius as the weighting factor.

Because it is important to ensure that no air bubbles are introduced thru the transport member 132 or through any seal to the adapter 170, it may also be desirable to measure the largest effective pore size of the capillary passage 176 between transport member 132 and adapter 170. This can be done using the above method to measuring the pore volume distribution of the transport member 132 alone and then measuring the pore volume distribution of the transport member 132 while attached to the adapter 170. The receding pore volume measured for the transport member 132 alone is then subtracted from the applicable pore grouping of the receding pore volume measured for the transport member 132 with adapter 170. The remaining cumulative pore volume distribution is then analyzed to determine the smallest pore radii with at least 95% of the saturated fluid retained in the pores. This smallest pore radii with at least 95% of the saturated fluid retained in the pores is defined as the largest effective pore size of the capillary passage 176.

The transport member 132 may be made of or include any suitable material. For example, the transport member may include fibers, woven fibers, sintered beads, foams, scrims and/or particles made from polymers or other materials. Essentra Porous Technologies or Porex are exemplary suppliers of transport members made sintering and fiber bundling processes. Exemplary polymers that have been found to be suitable include polyethylene, ultra-high molecular weight polyethelene (UHMW), polyethylene terephthalate (PET), nylon 6 (N6), polypropylene (PP), polyester fibers, ethyl vinyl acetate, polyether sulfone, polyvinylidene fluoride (PVDF), and polyethersulfone (PES), polytetrafluroethylene (PTFE), and combinations thereof. Other suitable materials include, but are not limited to, particulate metals and fibrous carbon. The transport member 132 may include a high density material such as, for example high density polyethylene (HDPE). It may be desirable for the transport member 132 to be free of or at least substantially free of polyurethane foam. Many ink jet cartridges include an open-cell polyurethane foam which can be incompatible with some fluid compositions, such as perfume compositions, and can break down over time when exposed thereto.

As shown in FIG. 5, the fluid transport member 132 may include an outer sleeve 185 that surrounds radial surfaces of the fluid transport member 132 along at least a portion of its length while keeping the first and second ends 160 and 162 of the fluid transport members 132 exposed. The sleeve 185 may be made from a non-porous material or a material that is less porous than the fluid transport member 132. The sleeve 185 may prevent or at least reduce air in the reservoir 130 from entering the fluid transport member 132 by radial flow.

The outer sleeve 185 may be a material that is wrapped around the fluid transport member 132 or may be formed on the fluid transport member 132. For instance, the material may be sprayed on the fluid transport member 132 or the fluid transport member 132 may be dipped into a fluid material that dries to form the outer sleeve 185. The outer sleeve 185 may be a polymer sheet, a Teflon tape, a thin plastic layer, or any other suitable material. Teflon tape has particular benefits since it provides a fluid-tight seal, is flexible to wrap, is strong, and also makes it easy to slip around the fluid transport member 132.

Priming the Refill

The cartridge 108 of the microfluidic delivery system 100 may be primed to remove air from the fluid path before inserting the cartridge 108 into the housing 102. Preferably, the fluid transport member 132 has capillary forces sufficient to pull the fluid from the reservoir 130 to the second end 162 of the transport member 132 and hold it there prior to and during use, thus self-priming. However, it may be desirable to prime the cartridge 108 by removing any air from the transport member 132, the filter 158, the lid 134, the slot 230 (if present) and the die 140. Priming may be performed by applying a vacuum force through the nozzles 188. The vacuum pressure is typically performed with the cartridge 108 in an upright position for a few seconds. In some embodiments, a vacuum force is applied for about 30 to about 60 seconds. The cartridge 108 may also be primed by applying air pressure through an opening in the lid 134 of the cartridge or the reservoir 130. Air or another pressurizing fluid can be supplied to increase the pressure on the fluid 122 in the reservoir 130, thereby pushing fluid 122 up the fluid transport member 132 through the fluid path.

The opening through which the pressurizing fluid is introduced into the reservoir may be sealed after priming. Further, the nozzles 188 may be sealed after priming to prevent de-priming of the cartridge 108 or evaporative loss of the fluid composition prior to the cartridge 108 being inserted into the housing of the microfluidic delivery system 100. An adhesive tape/label or cap with integral foam material can be used over nozzles 188 and vent hole to reduce losses due to evaporation as well as prevent de-priming of the cartridge 108. Alternatively or additionally, the cartridge 108 may be placed in a hermetically sealed bag or other structure. Further, the outer sleeve 185, if present, may help prevent de-priming of the fluid transport member 132. For example, the sleeve 185 may help prevent air from entering the fluid transport member 132 along its outer surface.

Operation of the Microfluidic Delivery System

As previously mentioned, the microfluidic delivery system 100 may deliver a fluid composition 122 from the cartridge 108 using thermal heating or other known fluid ejection devices. For example, the microfluidic delivery member 136 may include one or more heating elements. With non-limiting reference to the figures, fluid composition 122 contained within the reservoir 130 wicks up the transport member 132 toward the die 140 using capillary force. After passing through the second end portion 162 of the transport member 132 the fluid composition 122 travels through the filter 158, if present, through the aperture 149 in the lid 134, and into the die 140. The fluid composition 122 travels through the fluid channel 156 (for example, shown in FIG. 17) and into the inlet 184 (for example, shown in FIG. 12) of each fluid chamber 180. The fluid composition 122, which may comprise in part a volatile component, travels through each fluid chamber 180 to the heater 208 (for example, shown in FIG. 18) of each fluid chamber 180. The heater 208 vaporizes at least a portion of the volatile components in the fluid composition 122, causing a vapor bubble form. The expansion created by the vapor bubble causes a droplet of fluid composition 122 to be ejected through the orifice 190 of the nozzle 188. The vapor bubble then collapses and causes the droplet of fluid composition 122 to break away and release from the orifice 190 (for example, shown in FIG. 18). The system can be configured such that droplet of fluid composition 122 travels through the aperture 126 in the holder member 110, through the aperture 118 in the housing 102, and into the air. Fluid composition 122 then refills the fluid chamber 180 and the process may be repeated to release additional droplets of fluid composition 122. Other ejection processes may be used in addition or in the alternative to eject the fluid from the nozzle 130. For instance, piezoelectric elements or ultrasonic fluid ejection elements may be used to cause fluid to be ejected through the nozzles 188.

The output of the microfluidic delivery device 136 may be adjustable or programmable. For example, the timing between releases of droplets of fluid composition 122 from the microfluidic delivery system 100 may be any desired timing and can be predetermined or adjustable. Further, the flow rate of fluid composition released from the microfluidic delivery system 100 can be predetermined or adjustable. For example, the microfluidic delivery system 100 may be configured to deliver a predetermined amount of the fluid composition 122, such as a perfume, based on a room size or may be configured to be adjustable as desired by the user. For exemplary purposes only, the flow rate of fluid composition 122 released from the cartridge 108 could be in the range of about 5 to about 40 mg/hour or any other suitable rate or range.

Refilling the System

It may be desirable to refill the reservoir 130 once the fluid composition 122 has been used to a certain level. In systems where there is a removable cartridge 108, the spent cartridge 108 may be removed from the holder member 110 of the housing 102 and a new, or refilled, cartridge 108 may be inserted into the housing 102. The exact way the cartridge 108 is removed and/or replaced is not limiting. For example, the cartridge 108 may be inserted and removed from the holder member 110 of the housing by sliding the cartridge 108 in the direction generally normal to the direction the microfluidic delivery member 136 releases the fluid composition 122 into the air. The cartridge 108 may be connected with the housing 102 by sliding the cartridge 108 into the holder member 110 such that the reservoir 130 of the cartridge 108 connects with the bottom wall 114 and/or side wall(s) 116 of the holder member 110. The cartridge 108 may also connect with the top wall 112 of the holder member 110. The cartridge 108 may be connected with the holder member 110 in any suitable way. For example, the cartridge 108 or the holder member 110 may have a spring such that the cartridge is in a spring-loaded configuration when connected to the holder member 110. The system may have a release button to release the cartridge 108 or reservoir 130 from the holder member 110. Alternatively or in addition, the cartridge 108 or reservoir 130 may engage with a fastener to help secure it into the holder member 110.

The system may also provide for refilling by adding the fluid composition 122 to the reservoir 130, for example, through port 138 or by removing the lid 134 of the reservoir 130. In such cases, the reservoir 130 may be removable from the holder member 110 or permanently attached thereto. The port 138 may be sized to only accept very small filling devices, such as syringes, may include a 1-way valve or may have a stopper to help prevent the fluid composition 122 from leaking out of the reservoir 130 through the port 138. The fill port 138 can be located anywhere on the reservoir 130 or attached structure. The system may also include instructions for refilling the reservoir 130 and/or replacing the cartridge 108.

Fluid Composition

To operate satisfactorily in a microfluidic delivery system, many characteristics of a fluid composition are taken into consideration. Some factors include formulating fluids with viscosities that are optimal to emit from the microfluidic delivery member, formulating fluids with limited amounts or no suspended solids that would clog the microfluidic delivery member, formulating fluids to be sufficiently stable to not dry and clog the microfluidic delivery member, etc. Operating satisfactorily in a microfluidic delivery system, however, addresses only some of the requirements necessary for a fluid composition having more than 50 wt. % of a perfume mixture to atomize properly from a microfluidic delivery member and to be delivered effectively as an air freshening or malodor reducing composition.

The fluid composition of the present invention may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

In some embodiments, the fluid composition is free of suspended solids or solid particles existing in a mixture wherein particulate matter is dispersed within a liquid matrix. Free of suspended solids is distinguishable from dissolved solids that are characteristic of some perfume materials.

In some embodiments, the fluid composition of the present invention may comprise volatile materials. Exemplary volatile materials include perfume materials, volatile dyes, materials that function as insecticides, essential oils or materials that acts to condition, modify, or otherwise modify the environment (e.g. to assist with sleep, wake, respiratory health, and like conditions), deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

The volatile materials may be present in an amount greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%, by weight of the fluid composition.

The fluid composition may contain one or more volatile materials selected by the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

In the present invention, the fluid composition may have an average B.P. of less than 250° C., alternatively less than 225° C., alternatively less than 200° C., alternatively less than about 150° C., alternatively less than about 120° C., alternatively less than about 100° C., alternatively about 50° C. to about 200° C., alternatively about 110° C. to about 140° C. In some embodiments a quantity of low BP ingredients (<200 C) can be used to help higher BP formulations to be ejected. In one example, a formula with BP above 250° C. could be made to eject with good performance if 10-50% of the formula's ingredients has a B.P. less than 200° C. despite the overall average still being above 250° C.

In some embodiments, the fluid composition may comprise, consist essentially of, or consist of volatile perfume materials.

Tables 2 and 3 outline technical data on perfume materials suitable for the present invention. In one embodiment, approximately 10%, by weight of the composition, is ethanol which may be used as a diluent to reduce boiling point to a level less than 250° C. Flash point may be considered in choosing the perfume formulation as flash points less than 70° C. require special shipping and handling in some countries due to flammability. Hence, there may be advantages to formulate to higher flash points.

Table 2 lists some non-limiting, exemplary individual perfume materials suitable for the fluid composition of the present invention.

TABLE 2

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 3 shows an exemplary perfume mixture having a total B.P. less than 200° C.

TABLE 3

| CAS Number | Perfume Raw Material Name | Wt % | B.P. (° C.) |
|---|---|---|---|
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

When formulating fluid compositions for the present invention, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

In some embodiments, the fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present invention aid in the evaporation of perfume materials and may provide a hedonic, fragrance benefit. FPCs may be used in relatively large concentrations without negatively impacting perfume character of the overall composition. As such, in some embodiments, the fluid composition of the present invention may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition, in some embodiments, may be free of VOCs.

Perfume materials that are suitable as FPCs are disclosed in U.S. Pat. No. 8,338,346.

Throughout this specification, components referred to in the singular are to be understood as referring to both a single or plural of such component.

All percentages stated herein are by weight unless otherwise specified.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A microfluidic delivery device comprising:
   a reservoir that forms a hollow body with an opening, the reservoir having a reservoir volume;
   a transport member having a first end portion and a second end portion, wherein at least a portion of the first end portion of the transport member is in fluid communication with the reservoir, and wherein the transport member has a transport member volume;
   an enclosure at least partly closing the opening of the reservoir;
   a microfluidic delivery member comprising a microfluidic die, the microfluidic die having a fluid chamber in fluid communication with at least a portion of the second end portion of the transport member at an inlet of the fluid chamber, the microfluidic die also including a nozzle at an outlet of the fluid chamber; and
   an adapter disposed adjacent at least a portion of the second end portion of the transport member, the adapter having a wall that forms a cavity for receiving the second end portion of the transport member, wherein a capillary passage is formed at an interface between the wall of the adapter and the second end portion of the transport member, wherein the capillary passage has a largest effective pore size and wherein the transport member has an average effective pore size, and wherein the largest effective pore size of the capillary passage is smaller than the average effective pore size of the transport member,
   wherein the transport member volume is less than 60% of the reservoir volume.

2. The microfluidic delivery device of claim 1 wherein the transport member volume is less than 40% of the reservoir volume.

3. The microfluidic delivery device of claim 1 wherein the transport member volume is less than 20% of the reservoir volume.

4. The microfluidic delivery device of claim 1 wherein the transport member has a pore volume distribution with a receding pore volume of at least about 80% of the total volume in pores having radii less than about 150 um.

5. The microfluidic delivery device of claim 1 wherein the transport member has a pore volume distribution with a receding pore volume of at least about 80% of the total volume in pores having radii less than about 100 um.

6. A microfluidic delivery device comprising:
   a reservoir that forms a hollow body with an opening;
   a transport member having a first end portion and a second end, wherein at least a portion of the first end portion of the transport member is in fluid communication with the reservoir and has an average effective pore size;
   an enclosure at least partly closing the opening of the reservoir,
   a microfluidic delivery member comprising a die, the die having a fluid chamber in fluid communication with at least a portion of the second end portion of the transport member at an inlet of the fluid chamber, the microfluidic delivery member also including a nozzle at an outlet of the fluid chamber; and an adapter disposed adjacent at least a portion of the second end portion of the transport member, the adapter having a wall that forms a cavity for receiving the second end portion of the transport member, wherein a capillary passage is formed at an interface between the wall of the adapter and the second end portion of the transport member, wherein the capillary passage has a largest effective pore size, and wherein the largest effective pore size of the capillary passage is smaller than the average effective pore size of the transport member.

7. The device according to claim 6, wherein the adapter has a cavity width and the transport member has a transport member width, wherein the cavity width of the adapter is smaller than the transport member width such that the transport member is compressed at the second end portion when the transport member is disposed within the cavity.

8. The device of claim 6, wherein the reservoir includes a fluid composition.

9. The device according to claim 8, wherein a fluid composition travels through the transport member in a direction opposing the force of gravity when in use.

10. The device according to claim 8, wherein a fluid composition includes a volatile component.

11. The device according to claim 8, wherein the fluid composition comprises a perfume composition.

12. The device according to claim 6, wherein the transport member comprises polymer fibers or particles that are selected from the group consisting of polypropylene, polyethylene, polyester, and combinations thereof.

13. The device of claim 6 wherein the microfluidic delivery member includes a heater, piezo electric actuator or ultrasonic actuator.

14. The device of claim 6 wherein the reservoir includes at least a portion that is transparent or translucent.

15. An air freshening device including the device of claim 6.

16. The air freshener of claim 15 further including a housing having a holder into which the microfluidic delivery device is disposed during use.

17. The air freshener of claim 15 further including a power supply in adapted to electrically connect to the microfluidic device.

18. The air freshener of claim 15 wherein the microfluidic delivery device is disposable, refillable and/or rechargeable.

19. The air freshener of claim 15 having an output, wherein the microfluidic delivery device has an output and the output is adjustable by a user.

20. The air freshener of claim 19, wherein the output of the microfluidic delivery device can be adjusted by selecting a predetermined delivery rate for a particular room size.

21. A microfluidic delivery device comprising:
a reservoir that forms a hollow body with an opening;
a transport member having a first end portion and a second end portion, wherein at least a portion of the first end portion of the transport member is in fluid communication with the reservoir and the first end portion of the transport member has a first average effective pore size;
an enclosure at least partly closing the opening of the reservoir,
a microfluidic delivery member comprising a die, the die having a fluid chamber in fluid communication with at least a portion of the second end portion of the transport member at an inlet of the fluid chamber, the microfluidic delivery member also including a nozzle at an outlet of the fluid chamber; and an adapter disposed adjacent at least a portion of the second end portion of the transport member, the adapter having a wall that forms a cavity for receiving the second end portion of the transport member, wherein the adapter compresses at least a portion of the second end portion of the transport member such that the second end portion of the transport member has a second average effective pore size that is smaller than the first average effective pore size.

22. The device according to claim 21, wherein the reservoir includes a fluid perfume composition having a volatile component.

23. The device according to claim 21, wherein a fluid composition travels through the transport member in a direction opposing the force of gravity when in use.

24. The device of claim 21 wherein the microfluidic delivery member includes a heater, piezo electric actuator or ultrasonic actuator.

25. The device of claim 21 wherein the reservoir has a reservoir volume, wherein the transport member has a transport member volume and wherein the transport member volume is less than 60% of the reservoir volume.

26. The microfluidic delivery device of claim 22 wherein the transport member has a pore volume distribution with the receding pore volume of at least about 80% of the total volume is in pores having radii less than about 200 um.

27. The microfluidic delivery device of claim 21 wherein the capillary passage has a largest effective pore size and wherein the transport member has an average effective pore size, and wherein the largest effective pore size of the capillary passage is smaller than the average effective pore size of the transport member.

28. A microfluidic delivery device comprising:
a reservoir forming a hollow body with an opening, the hollow body of the reservoir defining a total volume;
a transport member having a first end portion and a second end portion, wherein at least a portion of the first end portion of the transport member is in fluid communication with the reservoir and a transport member volume;
an enclosure at least partly closing the opening of the reservoir forming an aperture,
a microfluidic delivery member disposed adjacent the aperture and including a die, the die having a fluid chamber in fluid communication with at least a portion of the second end portion of the transport member at an inlet of the fluid chamber, the microfluidic delivery member also including a nozzle at an outlet of the fluid chamber;
a filter disposed between the second end of the transport member and the microfluidic delivery member; and
a spacer between the filter and the microfluidic delivery member, wherein the spacer provides a gap between the microfluidic delivery member and the filter.

29. An air freshening device including the device of claim 28.

30. The air freshener of claim 29 further including a housing having a holder into which the microfluidic delivery device is disposed during use.

31. The air freshener of claim 29 further including a power supply in adapted to electrically connect to the microfluidic device.

32. The air freshener of claim 29 wherein the microfluidic delivery device is disposable, refillable and/or rechargeable.

33. The air freshener of claim 29 having an output, wherein the microfluidic delivery device has an output and the output is adjustable by a user.

34. The air freshener of claim 33, wherein the output of the microfluidic delivery device can be adjusted by selecting a predetermined delivery rate for a particular room size.

* * * * *